United States Patent
Roney

(10) Patent No.: US 9,615,786 B1
(45) Date of Patent: Apr. 11, 2017

(54) SOLO HOME USER SKIN IMAGING METHOD, ALIGNMENT AID, AND CHROMATIC FILTER FOR DETECTING GROWTH OF EARLY MELANOMAS

(71) Applicant: Sally E. Roney, Escondido, CA (US)

(72) Inventor: Sally E. Roney, Escondido, CA (US)

( * ) Notice: Subject to any disclaimer, the term of this patent is extended or adjusted under 35 U.S.C. 154(b) by 148 days.

(21) Appl. No.: 13/999,684

(22) Filed: Mar. 15, 2014

Related U.S. Application Data

(60) Provisional application No. 61/852,299, filed on Mar. 15, 2013.

(51) Int. Cl.
*A61B 5/00* (2006.01)
*G06T 7/00* (2006.01)
*H04N 1/107* (2006.01)

(52) U.S. Cl.
CPC ............ *A61B 5/444* (2013.01); *G06T 7/0014* (2013.01); *H04N 1/107* (2013.01); *G06T 2207/10008* (2013.01); *G06T 2207/30088* (2013.01)

(58) Field of Classification Search
CPC ....... A61B 5/441; A61B 5/444; G06T 7/0012; G06T 7/0014; G06T 7/0016; G06T 2207/30088; G06T 2207/30096
USPC ........ 348/77; 396/14, 15; 600/476, 477, 306
See application file for complete search history.

(56) References Cited

U.S. PATENT DOCUMENTS

| | | |
|---|---|---|
| 4,585,334 A | 4/1986 | Malyon |
| 5,241,468 A | 8/1993 | Kenet |
| 5,475,505 A | 12/1995 | Minasian |
| 6,215,893 B1 | 4/2001 | Leshem et al. |
| 6,233,064 B1 | 5/2001 | Griffin |
| 6,271,939 B1 * | 8/2001 | Hu ...................... H04N 1/00538 358/473 |
| 6,427,022 B1 * | 7/2002 | Craine ................. A61B 5/0059 128/922 |
| 6,661,539 B1 | 12/2003 | Nee |
| 7,104,450 B2 | 9/2006 | Khovaylo |
| 7,162,063 B1 | 1/2007 | Craine et al. |
| 7,359,748 B1 | 4/2008 | Drugge |
| 7,415,143 B2 | 8/2008 | Grichnik |
| 7,466,462 B2 * | 12/2008 | Chen ........................ H04N 1/10 358/471 |
| 7,657,101 B2 * | 2/2010 | Christiansen, II ... A61B 5/0059 382/118 |
| 7,779,569 B2 | 8/2010 | Riley et al. |
| 7,894,651 B2 * | 2/2011 | Gutkowicz-Krusin ................. A61B 5/0059 382/128 |

(Continued)

OTHER PUBLICATIONS

FAQs on the website of DermAlert (U.S. Pat. No. 7,162,063), http://www.dermalert.com, Mar. 16, 2013, http://www.dermalert.com/main/dermfaq.asp#3.

*Primary Examiner* — John Villecco

(57) ABSTRACT

An affordable method appropriate even for solo home-users without a partner to image their skin even in areas that they cannot see directly, or photograph. The method uses a device in contact with the skin to create images, and physical aids for consistently aligning the images. This permits comparison with later images to find growing lesions. The purpose includes the early detection of possible pre-melanomas and melanomas so diagnosis and treatment can be sought earlier. The images provide reliable proof of growth, a symptom, for the dermatologist's diagnosis. Alternately, a single set of easily referenced baseline images can be created.

16 Claims, 12 Drawing Sheets

(56) References Cited

U.S. PATENT DOCUMENTS

| | | | |
|---|---|---|---|
| 8,009,884 B2 | 8/2011 | Chio | |
| 8,109,875 B2 | 2/2012 | Gizewski | |
| 8,265,359 B2 | 9/2012 | Andrushkiw et al. | |
| 8,467,583 B2 | 6/2013 | Smith et al. | |
| 8,953,837 B2 * | 2/2015 | Gilad-Gilor | A61B 5/00 382/100 |
| 2002/0065452 A1 | 5/2002 | Bazin et al. | |
| 2002/0065456 A1 | 5/2002 | Bazin et al. | |
| 2003/0059127 A1 * | 3/2003 | Khovaylo | G06K 7/084 382/321 |
| 2004/0233480 A1 * | 11/2004 | Tehrani | H04N 1/00525 358/474 |
| 2008/0194928 A1 | 8/2008 | Bandic et al. | |
| 2009/0220415 A1 * | 9/2009 | Shachaf | A61B 5/0071 424/1.11 |
| 2009/0304243 A1 * | 12/2009 | Mertz | A61B 5/444 382/128 |
| 2010/0271470 A1 * | 10/2010 | Stephan | A61B 5/0077 348/77 |
| 2011/0210984 A1 * | 9/2011 | Wojton | A61B 5/444 345/634 |
| 2011/0213224 A1 * | 9/2011 | Merchant | A61B 5/0077 600/306 |
| 2011/0273535 A1 * | 11/2011 | Mendelson | A61B 5/444 348/43 |
| 2012/0008838 A1 * | 1/2012 | Guyon | G06F 19/345 382/128 |
| 2012/0172685 A1 * | 7/2012 | Gilbert | A61B 5/0059 600/306 |
| 2013/0137991 A1 * | 5/2013 | Fright | A61B 5/0077 600/476 |
| 2013/0225969 A1 * | 8/2013 | Bao | A61B 5/444 600/407 |
| 2013/0245417 A1 * | 9/2013 | Spector | A61B 5/0013 600/407 |
| 2013/0322711 A1 * | 12/2013 | Schultz | G06F 19/3418 382/128 |
| 2014/0039451 A1 * | 2/2014 | Bangera | G06F 17/5086 604/506 |
| 2014/0121532 A1 * | 5/2014 | O'Connor | A61B 5/0064 600/476 |
| 2014/0316235 A1 * | 10/2014 | Davis | A61B 5/7246 600/407 |
| 2014/0330130 A1 * | 11/2014 | Arneberg | A61B 5/0476 600/476 |
| 2014/0378810 A1 * | 12/2014 | Davis | G06T 5/40 600/407 |
| 2015/0025343 A1 * | 1/2015 | Gareau | A61B 5/6898 600/328 |
| 2015/0182757 A1 * | 7/2015 | Levine | A61B 18/203 601/46 |
| 2015/0230712 A1 * | 8/2015 | Aarabi | A61B 5/0077 600/476 |

* cited by examiner

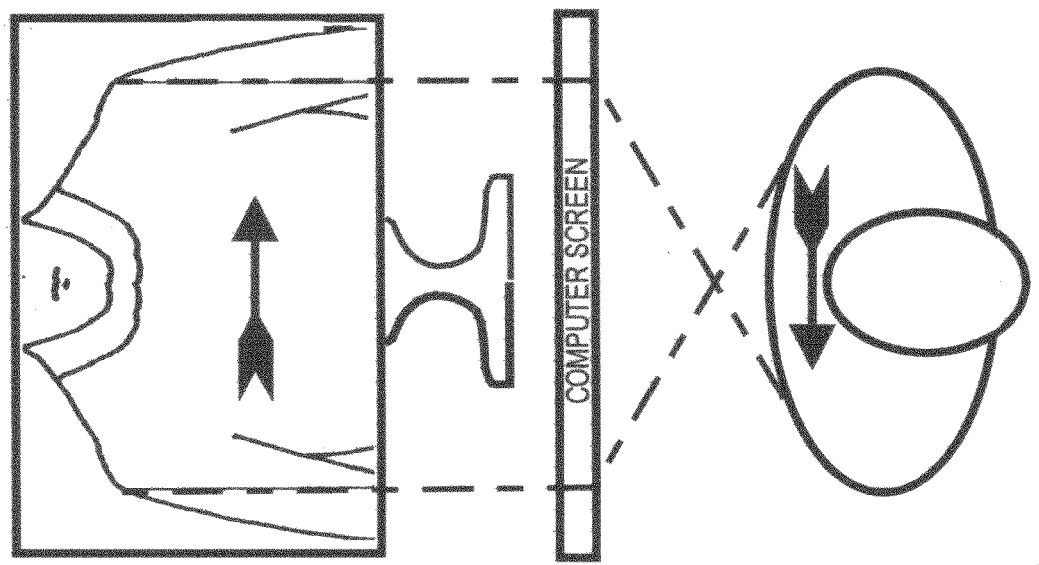
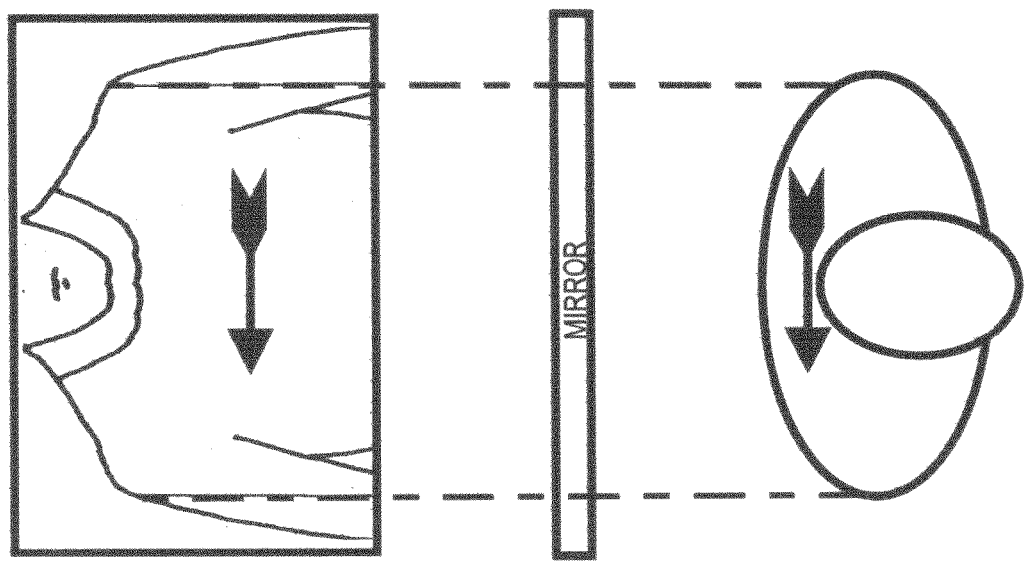
Fig. 3

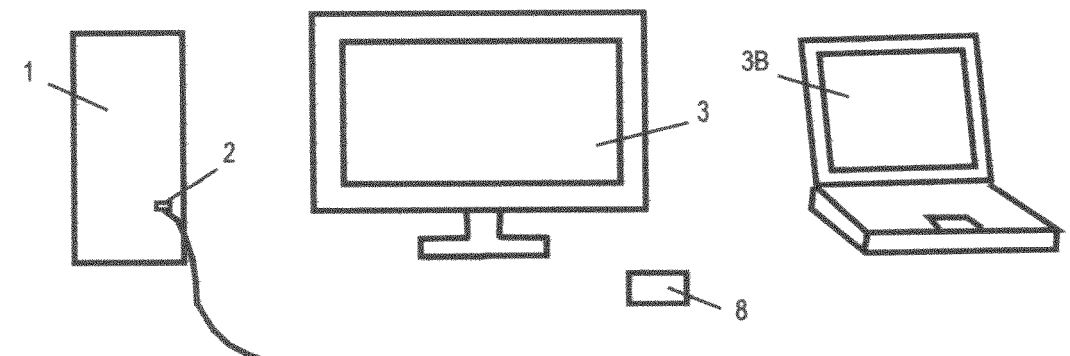
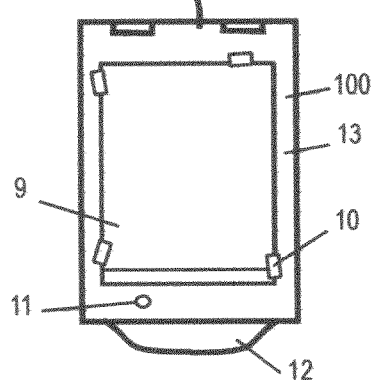
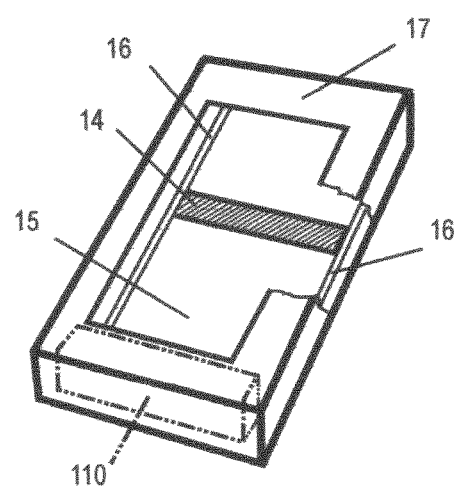
Fig. 4
Fig. 5
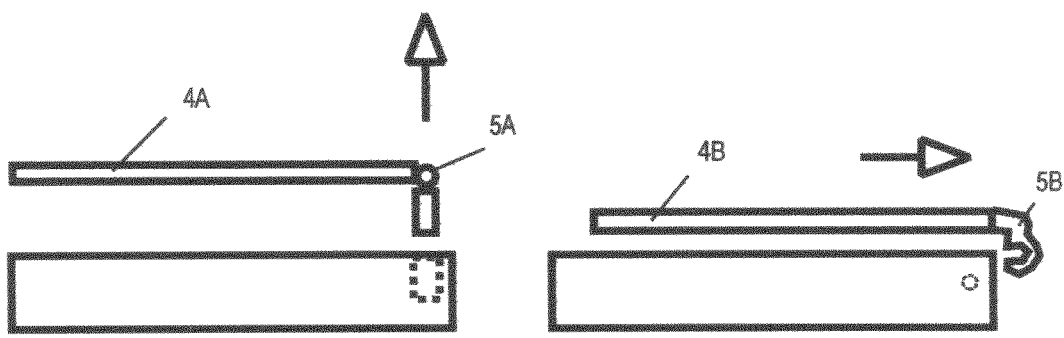
Fig. 6

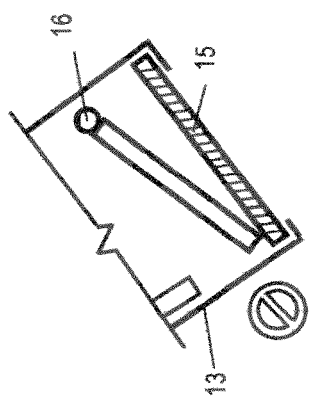
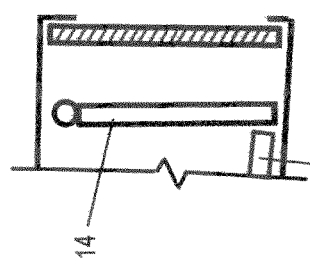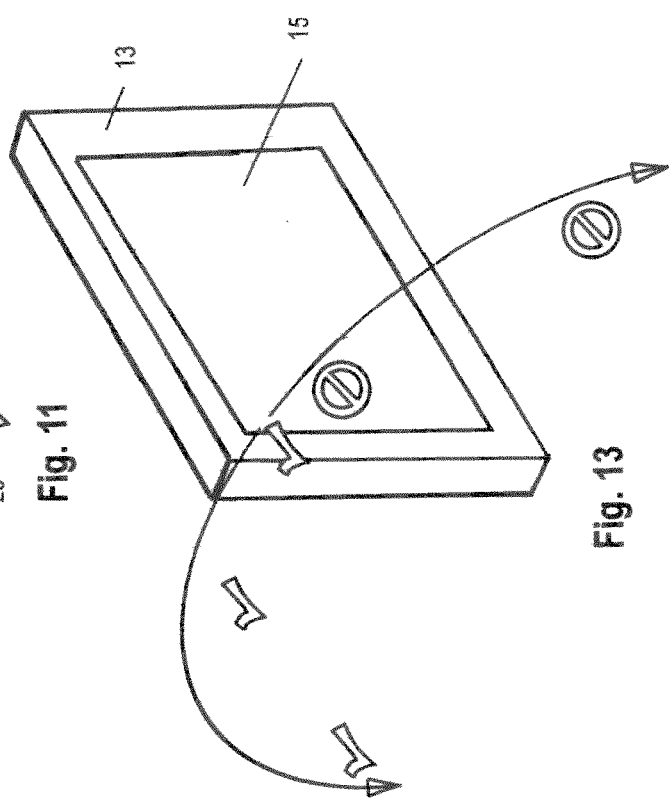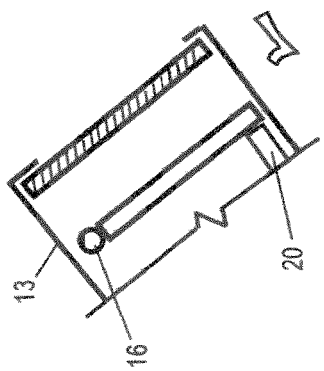

Copyright © 2012 Sally Roney

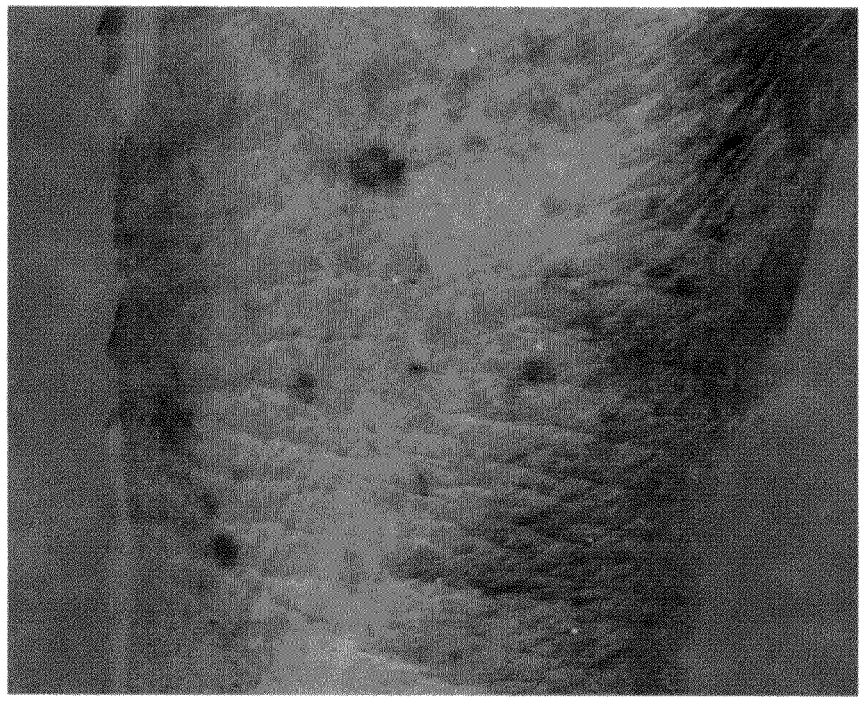
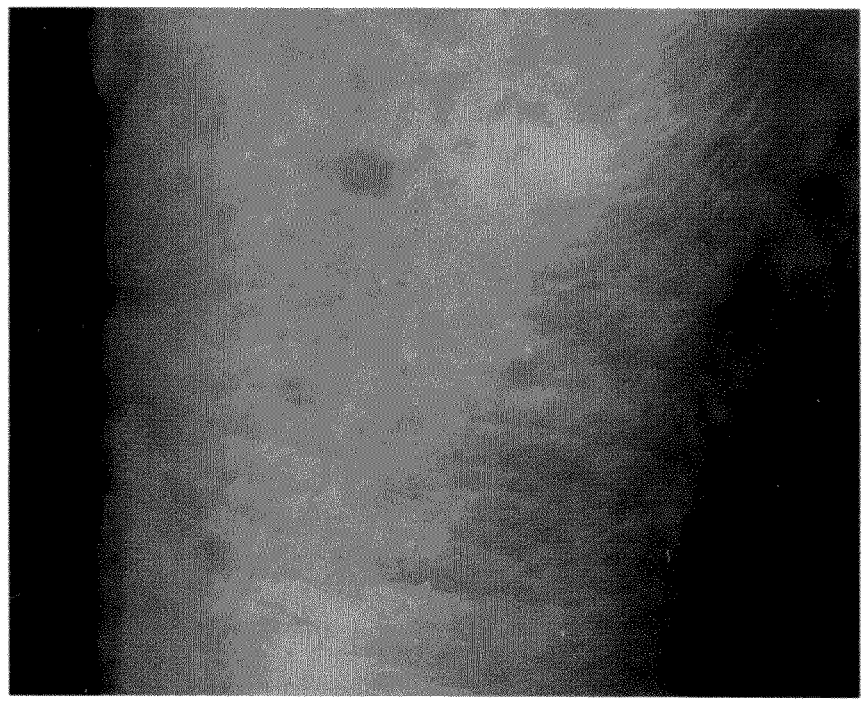
Fig. 22

SOLO HOME USER SKIN IMAGING METHOD, ALIGNMENT AID, AND CHROMATIC FILTER FOR DETECTING GROWTH OF EARLY MELANOMAS

CROSS-REFERENCE TO RELATED APPLICATION

This application claims the benefit of U.S. Provisional Application Ser. No. 61/852,299, filed 2013 Mar. 15 by the present inventor under the First-to-Invent Rule, which is incorporated by reference.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FEDERALLY SPONSORED RESEARCH OR DEVELOPMENT

Not Applicable

SEQUENCE LISTING, A TABLE, OR A COMPUTER PROGRAM LISTING COMPACT DISC APPENDIX

Not Applicable

REFERENCES CITED

U.S. Patent Documents

U.S. Pat. No. 7,162,063 B1 Jan. 2007 Craine, et al.
U.S. Pat. No. 7,104,450 B2 Sep. 2006 Khovaylo
U.S. Pat. No. 7,415,143 B2 Aug. 2008 Grichnik
U.S. Pat. No. 7,359,748 B1 Apr. 2008 Drugge
US20020065456 May 2002 Bazin, Roland, et al.

BACKGROUND

People have long been encouraged to take photographs for reasons of comparison. Although the difference between age spots and moles are not visible to an untrained home-user, moles grow and the age spot cannot grow. Therefore, the layperson does not need to be able to diagnose the difference. All they have to detect is a lesion getting larger.

The challenge is not in the ability of doctors diagnosing individual moles, but the gross problem of having patients unable to discover the suspicious lesions when they are located where they cannot be seen. This is most of the body when looking for pale lesions. In their early stages, melanomas can be blond. The purpose is not to diagnose but to focus the end-users attention on possible melanomas and give them documentation of growth that may allow them to receive earlier treatment.

Prior art is also what occurs in the 15 minutes doctors skin inspection. Size of lesions larger than 6 mm or one-quarter of an inch is used to indicate growth. This method does not require growth to that size before the suspicion of likely melanoma because growth can be quantitatively demonstrated to the dermatologist. The patient's vague anecdotal recollections of previous size are not always given credence. This evidence forms a basis for the dermatologists to remove the pre-melanoma earlier since the existence of a rapidly changing mole is a strong indicator of melanoma. Moles in contact with a scanner's glass platen are automatically at the same scale, unlike photographs.

Handheld scanners intended for dermatologists are expensive for home-users. If a patient is not in possession of their own data, their baseline may be unavailable in 20 years. Handheld spot-only scanners for consumers do not document bare mole-free areas. None of the prior art that only documents and analyzes lesion-by-lesion offers this advantage. Many moles generally are found on skin with no pre-existing mole.

Photo enclosures do whole-body scans but are not a home-user solution. This embodiment is not as quick, but some people may prefer it since it is less expensive, less intrusive and more private. Suspicious lesions can be monitored frequently at very high magnification at any time. The baseline record does not depend on finding the same business decades later.

The difference between this and fractal analysis, fractal analysis is not making a record of the entire body for baseline purposes. It diagnoses a particular mole as melanoma or non-melanoma. This prior art does not function as a baseline record, nor as a body wide survey of the current condition.

U.S. Pat. No. 7,415,143 uses a computer to scan for irregular growth. Selfscan uses fractal analysis. This method images and leaves detection to the user and diagnosis to their dermatologist; it may generate more found suspicious lesions for submission to these services.

Cameras

The FAQs on the website of DermAlert (U.S. Pat. No. 7,162,063) states that the method cannot be done without a partner. This makes sense since a partner is required to align the images in the camera's viewfinder. A person cannot be in front of and behind a camera at the same time. Since the scanner method can be done solo, this shows that it is not a direct substitution.

With a scanner, only one person is required to align his or her own body. The scanner allows solo usage because the person does not need to be both behind and in front of the device at the same time. Since one method requires two people and the other requires only one person, it cannot be considered to be done in the same way. Another difference is that the image on the viewfinder does not become part of the camera's digital image. Whereas U.S. Pat. No. 7,162,063's semi-transparent image on a scanner would become part of the digital image obscuring the skin. This is a different result. Taking photographs of moles has a long history in the traditional method.

The camera methods require calibration, scaling, between the baseline and current, while the scanner does not because it innately scans the images at the same scale.

Another problem with the camera for a solo user is the foreshortening.

U.S. Pat. No. 7,162,063 describes downloading from the camera to the computer. A scanner does not download because it is integral with the computer system. Its images are not stored on a memory card from which it needs to be downloaded. The information from the scanner goes directly into the computer's 1 memory 108 without being subjected to lossy JPG compression. This is why such very high-resolution images and large non-compressed non-lossy files are possible with the scanner.

COMPRESSION. JPG is a lossy format. A faint yellowish blond pre-melanoma, or its fractal dots, may be lost as a subtle difference during a camera's compression to the JPG file format. JPG compression is designed to look for light/ dark contrast appropriate for landscapes and portraits. Camera manufacturers try to store as many photos per storage card as possible. Amateur cameras automatically compress into lossy jpgs in order to load many images on to the card in the camera. Therefore, even if a camera offers a TIFF or bitmap option often that is just a change of format from a JPEG that has already degraded (blurred) the details of the image. Many cameras' software does not even offer the option to convert to TIFF or bitmaps. What is of interest here is the details not the overall image. Subtle color shifts differentiate pale-blond colored pre-melanomas from the skin color. Simplification could obscure fractal patterns at the edges.

The method of U.S. Pat. No. 7,162,063 requires alignment for each mole on the view thereby realigning and rotating these lossy jpg images many times. Each alignment degrades the image further, whereas the scan taken natively as a bitmap does not degrade from realignment.

Better Magnification.

The scanner can produce higher resolution images so this is a different result. The high-resolution images give better magnification which is very important for people with reduced visual acuity. An advantage of scanners over cameras is that they optionally allow just a small rectangle to be scanned. This reduces the detail's file size, yet allows magnification. The 4× magnification is very useful for a suspicious mole with a developing fractal pattern at its edges. This is a very bad sign. A fractal pattern is an organized "scattered" pattern of dots. The size of the dots is a third of the size of a period or larger. If the pre-melanoma is pale-blond, these tiny dots are blond too. This makes them harder to see. As the melanoma forms, tiny precise pinpricks of jet black can appear. The high-risk age group, middle aged to elderly, typically includes those with bad close vision. Even old scanners can be set to scan at higher samples per inch (i.e. more magnification) than even people with visual acuity problems would need. Although most users would not choose to use such very high resolution for all scans, it is helpful to have that option for suspected lesions FIG. 1 shows the overlaid outlines of three images taken by a 12-megapixel camera, a scanner at 300 spi, and a scanner at 1200 spi. All are shown at 100% resolution. The true size of the mole is shown to the left. Note the camera view (as shown in U.S. Pat. No. 7,162,063's back of a standing person) tries to shoot a large area so that those 12 megapixels have to cover many square inches of skin. The images seem larger on a monitor only because it is a coarse surface like a mosaic or a rough impressionist canvas, which only seems as good as a photo because we view it from a distance.

If the scanner were set to only 300 spi (samples per inch), it would print a full size photo at 100% magnification. A 3.2 mm or ⅛-inch mole would be shown as 3.2 mm or ⅛ inch in the printed photo.

If the scanner were set to 1200 spi, it would print a full size photo at 400% magnification. A 3.2 mm or ⅛-inch mole would be shown as 12.8 mm or a half-inch in the printed photo. That 2.54 cm or one inch of skin would appear on that monitor as 31.8 cm or 12.5 inches. The scanner allows just a small rectangle to be scanned. This is useful for a suspicious mole with a developing fractal pattern at its edges or for the visually impaired. Many scanners can be set to scan at higher samples per inch (i.e. more magnification) than even people with visual acuity problems would need. Although most users would not choose to use such very high resolution for all scans, it is helpful to have that option for suspected lesions.

View Confusion.

When the pre-melanomas are pale yellow instead of black, they can get lost in the confusion of an overly large complex image. What if a camera tried to take scan-sized images? Using cameras to take close-up photos of body parts to improve resolution, at the risk of overexposure, loses the context of the body part. Not all images contain a frame of reference. For example: a section of a forearm. FIG. 2. Even though software in U.S. Pat. No. 7,162,063 names the image file, it is up to the user to sort and identify the image.

If one tried to shoot too close trying to get a scan size image, the flash could wash out the exposure and the details of moles, as well as entire pale moles, could disappear. The scanner has a less bright light on the scanning head that moves with the scanner's internal camera, preventing it from overexposing the image. Professional cameras with controlled lighting such as U.S. Pat. No. 7,359,748 high-resolution cameras probably give excellent results. However, this is not a solo home-user solution. Home-user solutions must consider the typical knowledge of photography and the effects of close flash exposure by the home-user. Automatic exposure on camera is not intended to feature spots on skin but of faces and landscapes.

MIRROR CONFUSION is shown in FIG. 3. When a monitor displays the front view of a shoulder then the image appears to represent the opposite shoulder. If the user went to a mirror to compare, they would compare the body part from the wrong side. FIG. 3. The body part may not be identifiable since people are used to looking in mirrors. Seeing oneself on a computer display one subconsciously anticipates the image one would see looking into a mirror. The body part may not be recognizable since people are used to looking in mirrors. Is it the right arm or the left arm? If a surface, is it the outer surfaces or the inner surface? This is true with a camera image also. Even contextual views may not help camera users if taking the front or sides of the body. FIG. 2. Then the right arm is shown on the left side. From the back view, the right arm is on the right side. FIG. 3.

Professional workers do not find the location on the body using mirrors, so the unlabeled images are not confusing to them. Unexpected difficulties of recognizing left or right side body parts when imaged from the front and sides is an unexpected problem for home-users accustomed to mirrors.

For a front view, they see the right side of their body displayed on the left half of the screen rather than a mirror that would display the left half on that same side of the mirror. When taking an image of the back the right side of the body will appear on the right half of the display. For different views, the orientation will change. This can be very confusing for users of digital images taken by cameras or scanners.

It is necessary for the user to be able to locate actual locations on the body from these images. They need to inspect the original site, and to point it out to the doctor. However, baseline and current images can be compared for growth without any reference to actual location. A person cannot look directly at many portions of the body. These they can only see in a mirror. When a monitor displays a front view of a shoulder then the image appears to represent the opposite shoulder. If the user went to a mirror to compare, they would compare the body part from the wrong side.

Further confusion: some body parts such as forearms or hands are compared without mirrors since they can be seen directly. This is confusing if one tried using a mnemonic such as 'back views seem normal, but front & side views seem reversed'.

This confusion could also be partially solved by automatically converting images to mirrored images for only the views the user would need to use a mirror to see. However, this has the disadvantage of producing confusing images for the dermatologist who would not be using a mirror.

Advantages

Unique difficulties that the method solves are:

Solo operation to image areas the solo user cannot see or photograph. It eliminates the need for a second person, the photographer, in an embarrassing situation. Parts of the body that cannot be seen directly can be easily scanned.

The unusual method of using the scanner makes it easier and quicker than expected.

It solves the need to make affordable, high quality, scaled images and to be able to do it solo at home and as frequently as desired.

This method solves an unrecognized problem. The prior art camera methods' images are not easily recognized on a computer monitor because people are used to using mirrors. It is the old "my left or your left" conversation when standing face-to-face. To compensate camera views must show only the back view for Left-Right uniformity. To show body context they are forced to show large areas of the body. These distant views reduce the possible magnification. This method allows higher magnification close-ups that avoid body part confusion. FIG. 2.

Unlike cameras, it utilizes the scanner's inherently self-scaled images that are independent of user error. This is reliable proof of growth the dermatologist can trust.

It is an affordable in-home method in a field of mostly large expensive professional devices.

It allows a high-risk home-user, to monitor their own skin on their own schedule.

Using a scanner instead of a camera provides an option for very high-resolution images that can be displayed greatly magnified on-screen for people with visual problems.

The home-user has the advantage of deciding which scans to do. They feel empowered by being in control of the process.

This meets the long felt need for solo in-home operation offering privacy, convenience, and private long-term access to the baseline images. It avoids the need to be photographed in scanty clothing by a friend. It avoids the need to coordinate schedules with that friend.

This method allows for solo operation whereas camera methods do not.

Practical and affordable body digital images for solo home-users. In the High-risk middle age to elderly age group, a partner may not exist. The older user may not feel comfortable being photographed in scanty clothing by a friend or a child.

This method allows for aligned imaging of areas that would not be possible for the solo individual with a camera. These areas include:

The front, back and sides of the torso,
The back and sides of the thighs,
The back of the calves,
Front, back and sides of the upper arms,
Back of the neck,
Front and sides of face.

A method using an economical standard flatbed document scanner that people may already own.

Document scanners older than 10 years old have excellent resolutions and features. Even old scanners have the option of at least 1200 dpi, which have excellent resolution FIG. 1.

Mirror Confusion and View Confusion Aids.

This solo home method meets the needs of the high-risk users: diagnosed melanoma patients, the middle aged, and the elderly. Diagnosed patients require four times more frequent monitoring by their dermatologist due to their increased risk of forming additional melanomas. This disease tends to strike people 40 and older when close visual acuity declines.

Advantages over the two mirror solo home method:

Presents adequate magnification of almost all skin even if not directly visible. Thereby compensating for any loss of near vision to see fractal patterns and irregular edges, mimicking a high quality magnifying glass. In addition, this magnification is applied not only spot by spot, but the comparison between baseline and current images can be displayed at great magnification. This makes it easy to examine the entire body at magnification in a timely manner, rather than laboriously using a magnifying glass to focus on the entire surface.

For visual inspection of areas that cannot be viewed directly, it is recommended to use a mirror. However, by viewing in a mirror, one views from a distance equal to the distance to the mirror plus from the mirror, which is too far for close examination. It is difficult to compare previous size taken at a different distance between mirrors. The innate size calibration of the scanner, independent of user error, eliminates the need to guesstimate the size of moles when using a magnifying glass with a distant wall mirror.

Compensates for memory loss in remembering previous size, or even if mole previously existed, or false memory of previous existence during last inspection. The traditional two-mirror method makes it impossible to judge size changes. The two mirrors are held at different distances resulting in different size reflections. A 6-month-old memory of the size of a reflection of a mole may not be accurate.

In not directly visible areas: Loss of agility to use mirrors, or only distant views in mirrors, are a problem. As is difficulty to focus mirrors with magnification for each lesion. In this age group, a partner may not exist, or their eyesight or memory may be not any better.

Documents Mole-free Areas. All surfaces including bare skin without moles are imaged. Since most people over 18 years form few, if any, new benign moles, the images function as an inventory of pre-existing moles and their sizes, shape, color, and edges. In addition, they are an inventory of areas that contained no moles. Approximately one-third of melanomas form from skin with no moles. Spot by spot methods which only examine moles in isolation, do not document areas of skin that are free of moles.

Another embodiment records only baseline views. These act as a baseline reference even without continued scanning in order to identify future formation of melanomas even decades later. Since the images include areas that could not be viewed directly, the observer without this historical reference would have no remembrances of previous size, or even whether a mole previously existed, or whether they have a false memory of a previous existence. Demonstrated growth is an important symptom for Physicians.

Data Permanence

Data Permanence is another feature that is unique over all other prior art for digital images aligned with baseline images. This method creates baseline images that will probably be durable over decades despite changing operating systems. The data is in the possession of the home-user. The baseline images are standard common file formats that the user can convert to new file formats, along with their other data, if the old file format becomes obsolete. The images can be manipulated in a manual mode with basic simple operating system functions, which may change syntax, but will probably always exist. There is a manual method independent of any particular operating system. Some of the other prior art sells CDs of customer's data to them for storage; however the customer independently cannot create more for comparison. Therefore, the images would not be aligned. Others, including U.S. Pat. No. 7,162,063, use computer programs to sort, rename, and display but describe no manual method. A person's baseline may be made when they are eighteen and they may still be using that same baseline when they are 60. In the intervening years, they may not have felt themselves to be at sufficient risk to make any current comparisons. They may find themselves at age 60 discovering a lesion and wanting to check if that existed decades earlier.

Unlike spot-by-spot methods, the comparison method does not require identifying individual moles. This makes it faster to inspect the images, which makes it practical to inspect the entire surface of the body. It not only compares existing moles, but also verifies mole-free areas (in which one-third of melanomas develop) are still mole free.

The Ignored Scanner

If a device in contact with the skin such as a flatbed document scanner is so good for this, why did the prior art not use this before? It is because a person is not a sheet of paper. They are heavy, not as thin as a piece of paper and cannot easily hover above a flatbed document scanner, which will chatter if too much weight is applied. Prior Art in US20020065456 does not use this type of flatbed document scanner for other than the few obvious lightweight, easily positioned parts: hands, only two sides of the forearm, and the face. This is because other body parts would cause the flatbed document scanner to lug the motor, strip gears, produce unrecognizable images, or otherwise damage the flatbed document scanner. In addition, it would require bizarre body positions not suitable for older high-risk individuals.

One might think to enclose the flatbed document scanner in a protective case. However, unless that case were as big as a bed that would be a painful and slow way to scan the outer side of an upper thigh. A bed-sized case would not be practical for a home-user.

Some prior art uses a flatbed document scanner to create digital images from film photos or photo prints. This does not have the advantages of this method because: unless it is a professional quality close-up 8×10 film photo, it would not contain the same information as a true scan. Even then, the magnification would be limited. If it is a printed up version of a digital camera it has the same low quality image problems as the original. FIG. 1.

This is not a simple adaptation of the traditional recommendation to patients to periodically take photos for inspection.

Most flatbed document scanners 13 must be used in very different ways not mentioned in the prior art using cameras. In addition, a flatbed document scanner can produce different results not possible with a camera. Most significantly, it is what allows one person solo to take aligned images of parts of their body they cannot even see. In addition, camera close-up images are difficult to interpret for orientation while the flatbed document scanner can provide easily sorted unambiguous close-ups. This method of the first embodiment sounds easy and obvious, but some difficulties that it solves are:

It is hard to figure out how to scan some difficult views of one's body solo. Furthermore, those must be safe and convenient positions for people over 40.

Views need to be consistent for body position and for alignment. That is much more difficult than it would seem.

A unique feature quickly informs the occasional home-user how to scan consistent images of each view of the body.

This consistency allows these images to be taken in "good enough" alignment for rapid checking. If not carefully aligned a few may need one conventional photo editing software alignment to allow for rapid inspection. Verses multiple realignments required for images of large portions of the body containing a confusing multitude of lesions.

A seeming disadvantage of the first embodiment is one scans more views than if one stood back with a camera. However, this is actually an advantage for these reasons. When one includes too much information in a picture, one reduces the resolution of the skin in that image and can no longer zoom in to see detail. In addition, it is a very difficult to align hands, forearm, upper arm, and both sides in one image. In taking images of large areas of the body, it is hard to know if one has every view angle of arms and legs. By having more views, the problem of realigning digital images is reduced. Realigning a digital image takes longer than making a scan.

The method of the first embodiment uses a flatbed document scanner 13. Solo home-users can align and examine moles they cannot directly see. The advantage of this is the scale is innately calibrated by the flatbed document scanner 13. Thus, growth of lesions can be detected over time by the non-medical user. Therefore, the user can seek earlier preventive treatment.

GLOSSARY

"Enhanced pale-blond chromatic filter" or "Enhanced image 80 processing" see "yellow separation".

"Glass platen" 15 FIG. 5. The glass on top of flatbed document scanner 13.

"Long cord" refers to data cable 7 or data cable 7 with data extension cable 6. FIG. 4.

"Lossy" is a class of computer file formats that degrades the quality of its information by reorganizing itself to be smaller every time it changes. Lossless file formats do not.

"Means of opacity" or "a backing of a contrasting means of opacity" or an "opaque reflective shape 55". Examples: white ink, other colors of opaque ink or paint, labels.

Means of temporary adhesion. Examples: Repositionable tape 10, removable tape 10, repositionable glue.

"Methods of orienting", as relates to scanners, refers to the methods shown in the drawings and detailed in the specification section How Use & Hold Scanner 13. FIGS. 7 through 16.

"Mirror Confusion" refers to the confusion created by a monitor displaying body parts that seem to be of the other side of the body. FIG. 3.

Mirrored graphic is a symbol as it would be seen in a mirror. FIG. 19.

ppi. A computer screen 3 uses ppi (pixels per inch). Herein ppi is expressed as how concentrated those pixels are over the area of the skin they are describing.

Repositionable tape 10—removable tape 10 such as painter's tape or drafting tape.

"Scanning head" 14 FIG. 5. It is the moving bar under the glass platen. "Rail" 16 used herein is the bar to which scanning head 14 is connected. "Track" 20 as used herein is the surface that scanning head 14's free end rests upon.

"Sensory marker" is a temporary object that can be felt when not seen. For example: crumpled repositionable tape 10.

"spi" is samples per inch, much like dpi, dots per inch, for a printer, or ppi, pixels per inch, for a computer screen or camera. High resolution is like a mosaic of the same size but made up of smaller, more closely spaced, tiles or color data.

"Spot" herein refers to a mark in an image that is not yet diagnosed. If it never grows or changes, there is no need to diagnose it. It may be a mole or lesion or a scar or age spot.

"Suspicious lesions" include: lesions where there were not lesions before, lesions that have assumed a different shape, lesions that have increased in size.

The term, "Scanner" as used herein is not an expensive dermatologic hand-held scanner that accumulates images by hand movement of the scanner. Neither is it the spot-by-spot scanner sold to consumers to monitor only individual lesions. It is any maneuverable device that can image a surface while in contact instead of being aimed like a camera. For the first embodiment, it is a standard flatbed document scanner 13 not designed to scan in all orientations. For example: a single-rail 16 scanner 13 with motor 110 designed to scan while laying flat on a desk. FIG. 4 13.

The term, "vertical flatbed document scanner", as is included in the second embodiment, is a scanner such as in U.S. Pat. No. 7,104,450. This is a scanner designed for scanning in many orientations.

"View" refers to the visual range of a portion of the body that is contained in one particular image.

"View Confusion" is the lack of contextual clues to identify a body part or its orientation.

"view-specific information" or "view-specific template information" refers to information that has been particularized for one "view". This information include a subset of aids as listed under the heading "SCANNING AND ALIGNMENT AIDS" and shown in FIG. 17. These include view-specific instructions for positioning the body and orienting the scanner in a manner consistent with the methods shown in the drawings and detailed in the specification section "HOW TO USE & HOLD SCANNER 13". FIGS. 7 through 16.

"view-specific template." refers to a template with information that has been particularized for one "view".

SUMMARY

In accordance with one embodiment, this is an affordable method appropriate even for solo home-users without a partner. They can image their skin, even in areas that they cannot see directly, or photograph. The method uses a device in contact with the skin to create images. Aids consistently align the images. This permits comparison with later images to find growing lesions. The purpose includes the early detection of possible pre-melanomas and melanomas so diagnosis and treatment can be sought earlier. The user creates a baseline set of images and later compares them to current images to check for growth or changes. Alternatively, the user takes only the baseline images and uses them to quickly check if a casually noticed lesion is new or pre-existing. The device of the first embodiment can produce images better suited to this use than cameras. Intrinsic advantages include: solo usage, innate calibration, option of 4× magnification for the visually impaired, designed for better detail rendition rather than overall pleasing images, and the possibility for unambiguous close-ups.

BRIEF DESCRIPTION OF THE DRAWINGS

FIG. 3 illustrates Mirror Confusion:
FIG. 4 shows a possible setup for scanning.
FIG. 5 shows two-rail scanner 17.
FIG. 6 shows methods of removing scanner lids 4A & 4B.
FIG. 10 shows horizontally upright scanning using scanner 13 with its rail 16 side up, scanning head 14 is in a functional orientation with its free end resting in its track 20. It also shows scanning head 14 connection to rail 16 and scanning head's free end rests on track 20.
FIG. 11 shows horizontally upright scanning using scanner 13 with its rail 16 side up, at the limit of the functional orientation.
FIG. 12 shows scanner 13 with its rail 16 side up, in a non-functional orientation wherein scanning head 14 hits glass platen 15.
FIG. 13 shows functional range of orientations of scanner 13 for horizontally upright scanning using scanner 13 with rail 16 side up.
FIG. 22 shows full-size details from FIG. 20 and FIG. 21. Compare the two details to see the effect of the post-processing. The plurality of marks shown is (hopefully) age spots.

Drawings - Reference Numerals

Figure 1:
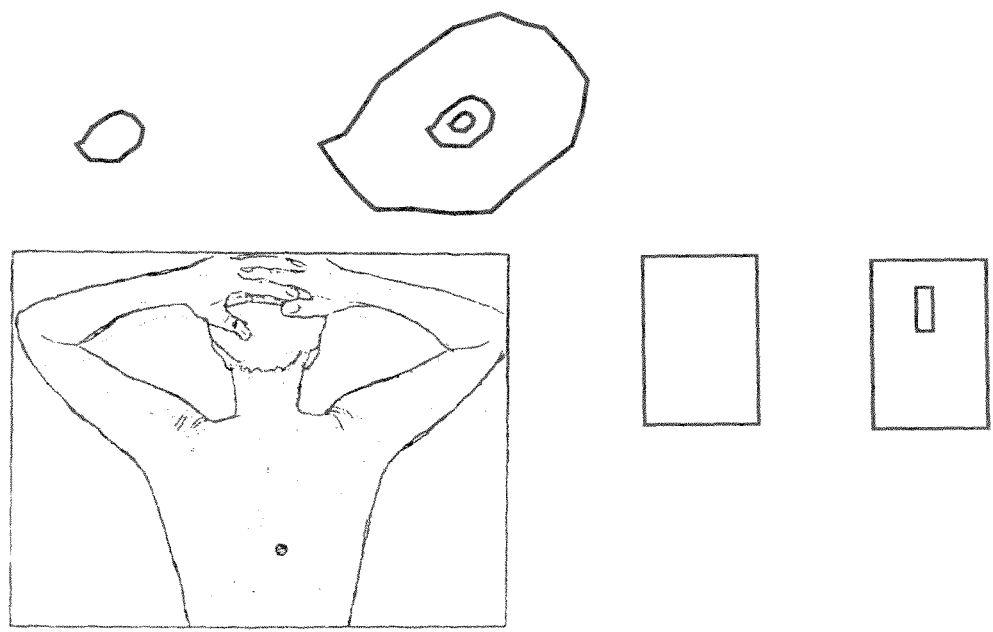
FIG. 1 compares resolution of scanner vs. camera.

| FIG. | # | |
|---|---|---|
| 4 | 1 | computer |
| 4 | 2 | port |
| 4 | 3 | screen |
| 4 | 3b | laptop |
| 6 | 4a | lid |
| 6 | 4b | lid |
| 6 | 5a | hinge |
| 6 | 5b | hinge |
| 4 | 6 | data extension cable |
| 4 | 7 | data cable, "Long cord", data cable 7 with data extension cable 6. |
| 4 | 8 | mouse |
| 4 | 9 | template 9, "View-Specific Video Instructions 122", "Scanning and Alignment Aids" |
| 4 | 10 | removable tape, Means of temporary adhesion. Repositionable tape 10 such as painter's tape or drafting tape, repositionable glue |
| 4 | 11 | scan button |
| 4 | 12 | handle |
| 4 | 13 | scanner |
| 5 | 14 | scanning head |
| 5 | 15 | glass platen |
| 5 | 16 | rail |
| 5 | 17 | scanner with two rails |
| 5 | 20 | track |
| 17 | 30 | Scan order, "Control of Workflow" |
| 17 | 31 | Icon for template orientation on glass platen |
| 17 | 32 | Arrow for up |
| 17 | 33 | Equipment symbol |
| 17 | 34 | Diagram of position |
| 17 | 35 | Custom physical label added by user for scanning |
| 17 | 36 | cell phone code |
| 17 | 37 | Body side for scanning |
| 17 | 38 | Thumbnail photo |
| 17 | 39 | Outline |
| 17 | 40 | Position instructions |
| 17 | 41 | View title for scanning |
| 17 | 42 | Orientation text for scanning |
| 18 | 50 | View Number |
| 18 | 51 | Body side |
| 18 | 52 | View title |
| 18 | 53 | Custom physical label added by user |
| 18 | 54 | Orientation labels |
| 18 | 55 | Opaque reflective shape, "Means of opacity", "a backing of a contrasting means of opacity" |
| 20 | 70 | Image as scanned |
| 21 | 80 | Enhanced image |
| 23 | 102 | tablet computer capable of display only |
| 23 | 105 | Tablet computer memory |
| 23 | 106 | Tablet computer processor |
| 23 | 107 | Personal computer |
| 23 | 108 | Personal computer memory |
| 23 | 109 | Personal computer processor |
| 5 | 110 | scanner motor |
| 21 | 112 | Disappearing Instructions, automatically disappears |

DETAILED DESCRIPTION OF FIRST EMBODIMENT

Introduction

This first embodiment is a method to help even solo home-users to find lesions that are growing without the need to diagnose, identify, or locate each lesion. This makes it faster to inspect, so that it is practical to inspect almost the entire surface of the body. Not only are existing moles documented, but also the mole-free areas in which one third of melanomas develop. Although a unique advantage is the ability to image solo in privacy, the aid of a second person, or even the imaging done as a service is possible.

This first embodiment method is for any device that can image a surface while in contact. This includes common home computer 1 with a standard flatbed document scanner 13, as will be discussed. This method uses equipment that the user may already own. Flatbed document scanners 13 are inexpensive, and have been available long enough that there are used ones available. No expensive specialized medical equipment is used. Most document scanners 13 require these holding methods.

This not only is a method it also has a physical aid to permit close alignment Without the aid, the images would not be aligned closely enough to allow comparison. Because there is no need to identify the location on the body, comparison is less time consuming.

Setup

Setup FIG. 4.

The setup consists of computer 1 with port 2 and screen 3 or 3b of FIG. 4, document scanner 13 with data cable 7 and optional data extension cable 6. Conventional pieces of furniture of various heights (not shown) are used to assume the various positions. A long data cable 7, or data cable 7 with data extension 6, is attached to scanner 13 for maneuverability and portability to reach the furniture (not shown).

Flatbed document scanners 13 usually have scan button 11 that can be used away from computer 1. Scanners' 13 own software driver generally can be set to display small images of the scans as they are taken.

Document scanner lid 4a or 4b of FIG. 6 is removed. Most document scanner lids 4a or 4b are removable; the others are easily cut at hinges 5a or 5b.

Templates 9

Templates 9 FIG. 4 for glass platen 15 FIG. 5 of flatbed document scanner 13 are made from standard stationary supply transparency sheets. Templates 9 contain printed organizational and Position instructions 40 and aids. The physical aids provided allow quicker, consistent scans without the need for the home-user to remember how. Templates 9 include outlines 39, position instructions 40 for each position, orientation, view identification and other labeling. Use means of temporary adhesion 10 FIG. 4, such as painter's tape or drafting tape, to hold templates 9 on glass platen 15.

Figure 17:
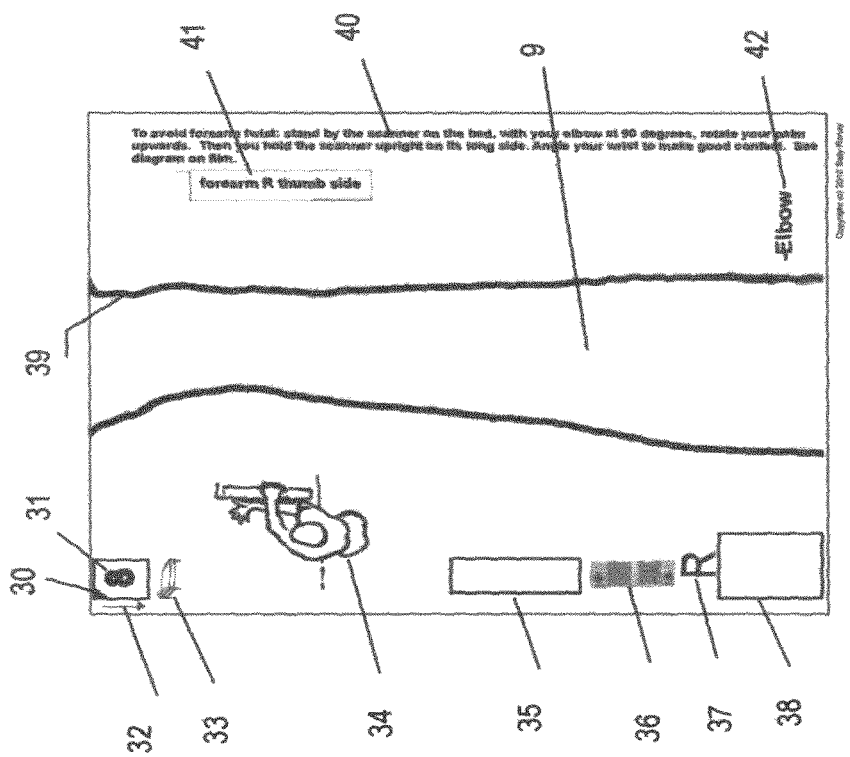
FIG. 17 shows some informational aids on a typical template 9 for body positioning, scanner orientation, workflow and other described aids. These are visible prior and during scanning. These disappear in digital images 70.

Scanning and Alignment Aids FIG. 17

I presently contemplate for this embodiment these sorts of symbols and text aids. Not all images require all these symbols and text aids. Many different symbols and text aids are possible.

View title 41 (Body part)—for quicker scanning (visible while scanning)

Body part alignment outline 39—for quicker and accurate scanning

Body Position instructions 40—for quicker and accurate scanning (invisible)

Body side for scanning 37—R/L—for quicker scanning

Orientation text 42—for accurate scanning

Thumbnail photo 38—for quicker scanning

Equipment symbol 33—for quicker scanning (invisible)

Diagram of position 34—for quicker scanning (invisible)

Icon 31 for template orientation on glass platen 15—for quicker and accurate scanning (invisible)

Scan order 30—for quicker scanning

Orientation Targets—for accurate scanning

Arrow 32 for up—helps orient for scans scanned inverted to make scanning easier

Alignment lines—extending from fingers to align them, not shown

Cell phone code 36 so that customers can access more detailed information or easier alternate views.

Custom physical label added by user for scanning 35

Alternatively or optionally, there could be sound, video, computer media displays, or booklets that relate the body position information. However, an advantage of on-template aids is that they are right there when they are needed.

Instructions

The method is possible because of the close alignment scans being taken months apart. Without template 9 alignment, comparison would be too time-consuming to be practical. Scan order 30 allows scans to be made in the quickest order, rather than the most seemingly logical order. Scan order saves time during scanning by using the same equipment setup and settings in the same location for successive scans.

The color of outline 39 is distinguishable from skin color. There are outlines 39 for different body types. Optionally, thumbnail photos 38 can be customized by the user. An outline 39 is not enough. Position instructions 40, diagrams, and written texts on template 9 allow the body part to assume consistent position with respect to joints and rotation.

The functionality of having the position text and diagrams on template 9 itself, include speed of use, and not having to remember how to hold the body part or scanner 13 for each of the views. Printed position instructions 40 and other aids on template 9 make it possible to scan in a reasonable amount of time. Since there are many views, if one had to look up in a book or watched video, the time to make these scans would be prohibitive.

Figure 21:
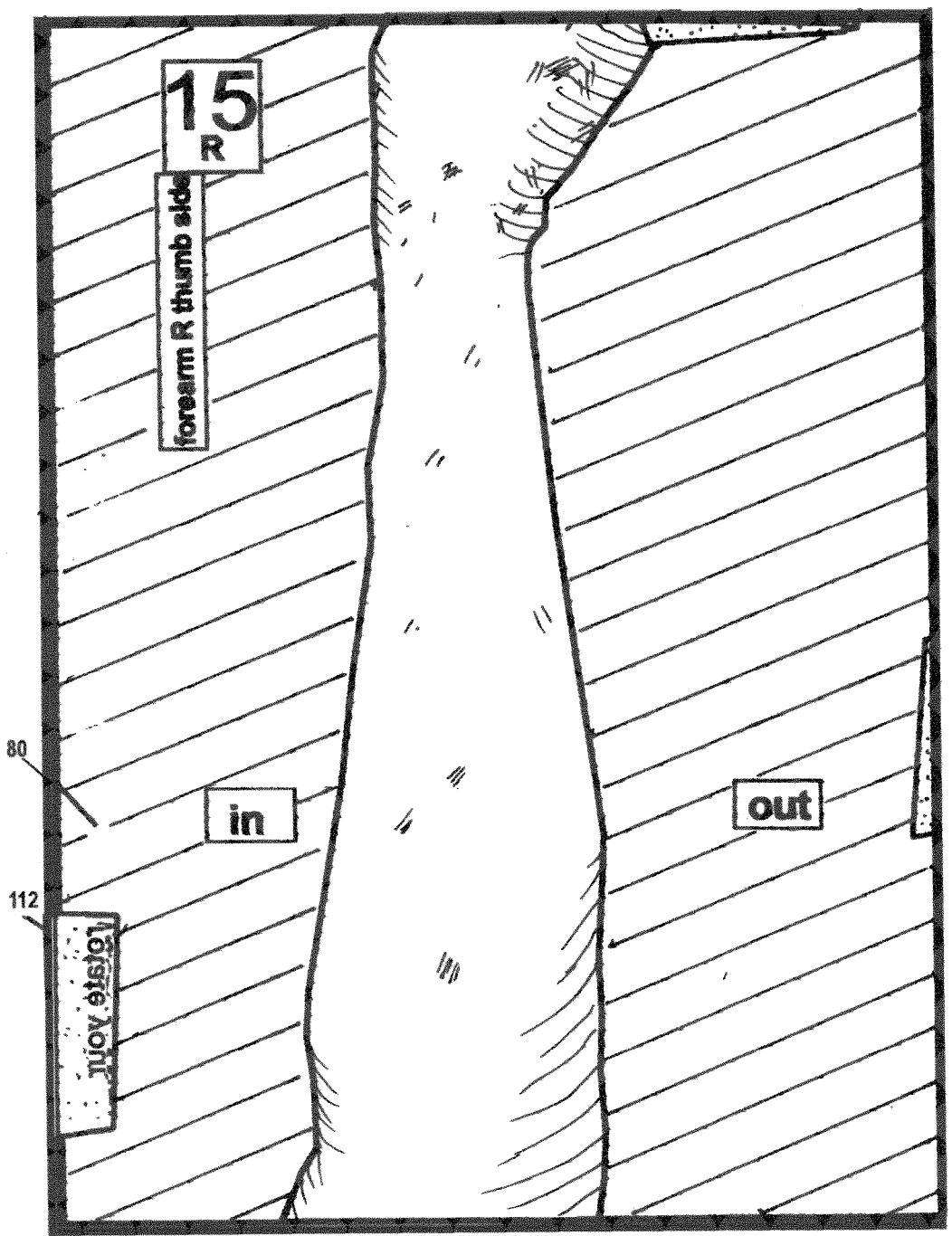
FIG. 21 shows a drawing of the enhanced pale-blond chromatic filtered image 80 of the same digital color image 70. Note disappearing instructions 112 are obscured in the blackness surrounding the body part as noted in the drawing. When the digital image is compared to a later enhanced pale-blond chromatic filtered image 80, a changing pattern could be detected.
Figure 23:
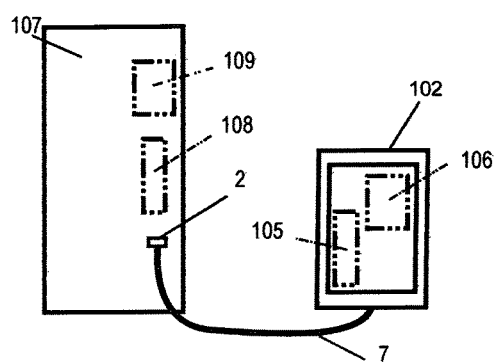
FIG. 23 shows tablet computer 102 that is not capable of processing images attached by data cable 7 to personal computer 107. Tablet computer's 102 memory 105 and processor 106 and personal computer's 107 memory 108 and processor 109 are exchanging stored images 70.

Disappearing Instructions 112. FIG. 21 Lower Left Edge.

Although the text can be seen during scanning, it does not become part of the image because it is in black text and the images are taken with lid 4a or 4b removed. Therefore, the background of the body part is black, and all the printed text that is not desired to show in the image disappears. Disappearing instructions 112 are useful in order to reduce distractions during the inspection.

Older computers and old scanners 13 can be used. A light or medium-tone scanner interior is recommended to illuminate the instructions. A black or dark grey scanner interior will be dimly lit. The current fashion is for black scanners 13. So users may be buying used scanners 13 rather than adapting the dark interior.

Disappearing instructions 112 quickly inform the occasional home-user how to scan consistent images of each appropriate-sized section of the body. Home-users do this a few times a year, unlike medical technicians who do it daily. The availability of instructions right there on template 9 reminds them how.

Mirrored Instructions

Figure 19:
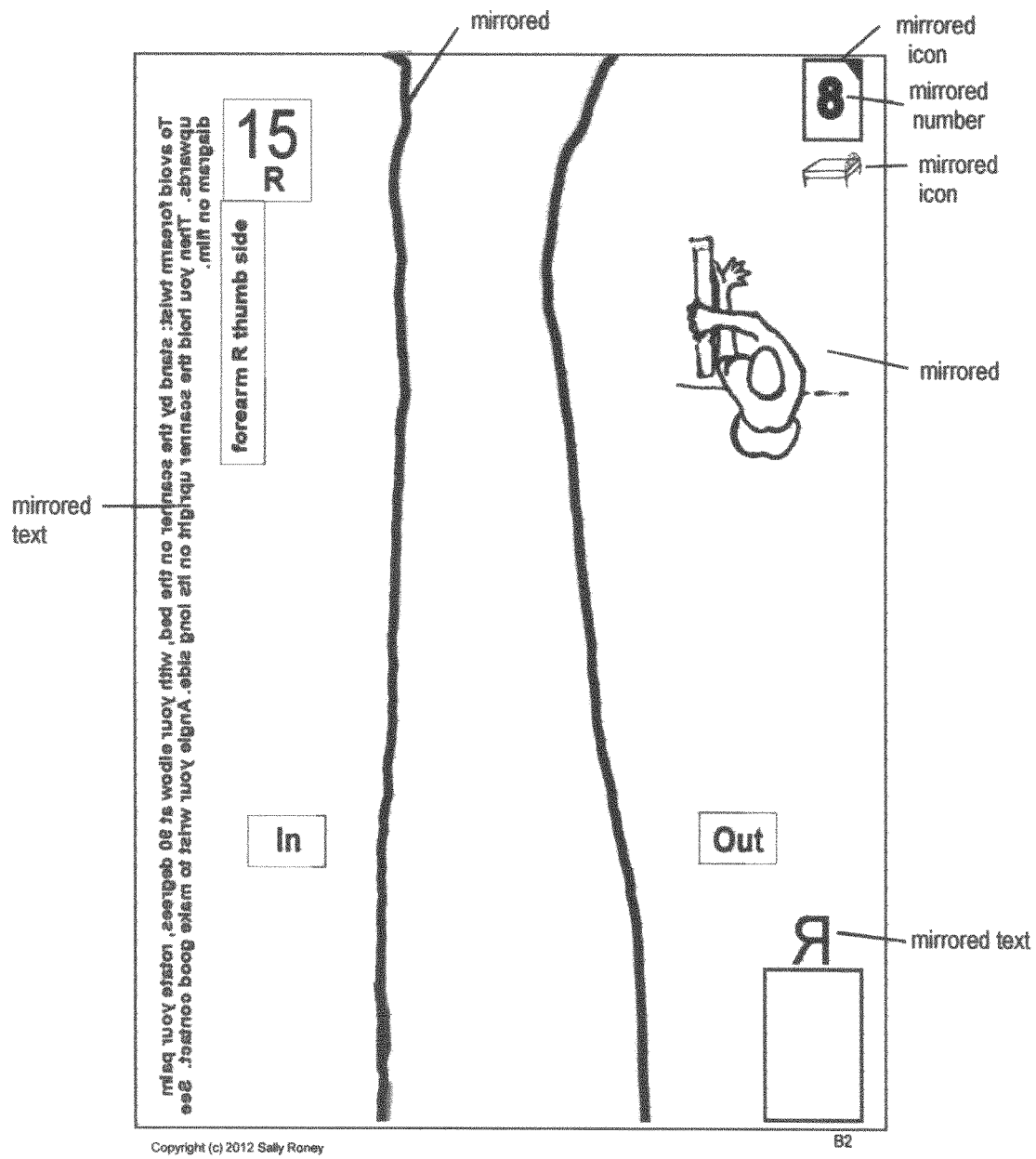
FIG. 19 shows mirrored and normal text as printed on underside of template 9.
Figure 20:
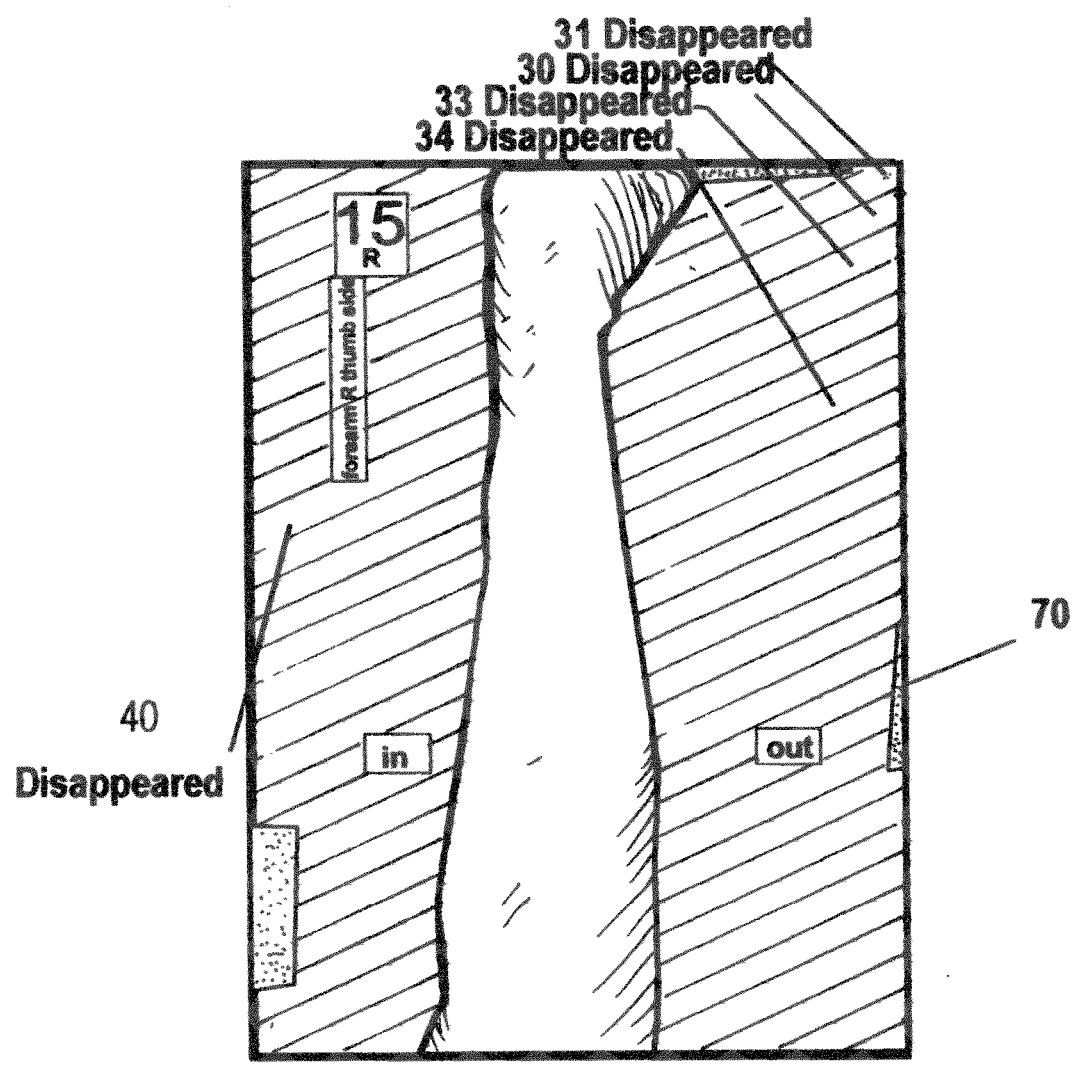
FIG. 20 shows a drawing of digital color image 70. Note the digital color image 70 is automatically calibrated, automatically labeled and automatically annotated and the aligning information has automatically disappeared 112.

The instruction's text and symbols to be viewed while scanning, are printed in mirrored text on the under surface of template 9 FIG. 19. Mirrored text is text as it would appear in a mirror. Thus, if seen from the other side of template 9 it would be normal text. Thus, the upper surface is cleanable. The mirrored text also eliminates the expense, and need to align two-sided printing. I presently contemplate for this embodiment using mirrored text; however it could also include instructions printed on the top of template 9 in normal text. However, that embodiment would not be cleanable.

Positions

Without position instructions 40 for body position, rotation and twisting of various body parts may prevent close enough alignment. Position instructions 40 describe a consistent position in which it is actually possible to make that scan. Surprisingly, the forearms are extremely difficult We twist our wrists without even thinking. Without detailed position instructions 40, consistent images could not be made. Outline 39 alone does not inform the user how to avoid twisting in the thumb side view of the forearm. A pair of orientation targets, conventional color-coding labels (not shown), are used to avoid wrist twist in the difficult forearm positions. Several joints naturally twist thereby showing a different of arrangement of moles. For views where position instructions 40 indicate orientation targets, apply one centered on the proper side of each end of the body part that can twist. Then assume the body position. Check that both targets are centered to prevent joint twist.

The method provides safe convenient positions for people over 40.

Automatic Labeling Appearing in the Images

Identification labeling text and symbols to be visible in the digital image are printed in regular text on the underside of template 9. I presently contemplate for this embodiment that opaque reflective shapes 55 would underlay the text; however, it could be printed in white text or on printed labels. Users can add labeling using printed labels. I presently contemplate for this embodiment these sorts of symbols and text labels. Not all images require all these symbols and text labels. Many different symbols and text labels are possible.

The resulting images contain helpful organizational information. For example:

View Number 50—for sorting (visible in digital image)

View title 52 (Body part)—for sorting (visible in digital image)

Orientation aids—for preventing view and mirror confusion (visible in digital image)

Body side 51—R/L—for preventing mirror confusion (visible in digital image)

Orientation labels 54—for interpretation and preventing view confusion (visible in digital image)

Custom physical label added by user 53 (visible in digital image)

Without Orientation, information identification of individual moles would not be practical. None of this labeling is possible with a camera. Orientation labels 54 and R/L body part labels are particularly useful for the user for preventing view and mirror confusion. Labeling of view numbers and titles allows scans to be made in the quickest order, Scan order 30, rather than the most seemingly logical order. This is only possible because the self-labeled images are so easy to sort.

View Confusion and Mirror Confusion Aids

This method meets the unrecognized need for images that are automatically labeled to avoid the confusion of seeming to be of the opposite side of the body. FIG. 3. When screen 3 displays the front view of a right shoulder, the image appears to represent the left shoulder. The body part may not be identifiable since people are used to looking in mirrors. Seeing oneself on computer screen 3, one subconsciously anticipates the image one would see looking into a mirror. If the user went to a mirror to compare, they would compare the body part from the wrong side. FIG. 3. The self-labeled images are so much easier to sort and to interpret.

This confusion is true with a camera image also. Seeing oneself on computer screen 3 one subconsciously anticipates the image one would see looking into a mirror. Instead, for a front view, they see the right side of their body displayed on the left half of screen 3. A mirror would display the right shoulder directly forward in the mirror on the right side. When taking an image of the back the right side of the body will appear on the right half of screen 3. For different views, the orientation will change. This can be very confusing for users of digital images taken by cameras or scanners 13. Without this self-labeling the user would have to envision the direction of the camera's eye relative to the direction of their own eye to know which side of screen 3 to look.

Although templates have been labeled in the past for patient name and other identifying information, this labeling is more useful because home-users need more instruction and orientation aids than professional workers daily doing the same thing do. Professional workers do not find the location on the body using mirrors, so the unlabeled images are not confusing to them. They look at the patient with the same eye direction as a camera would.

Orientation Labels 54

Figure 2:
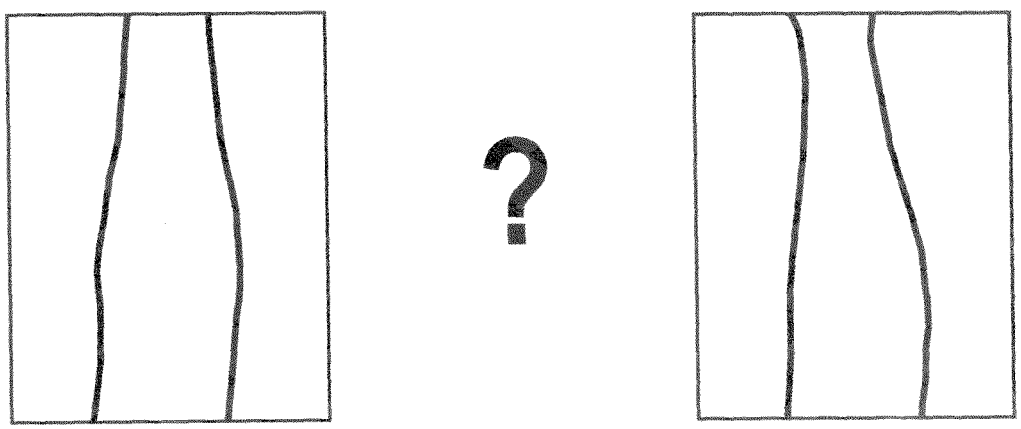
FIG. 2 illustrates View Confusion.
Figure 18:
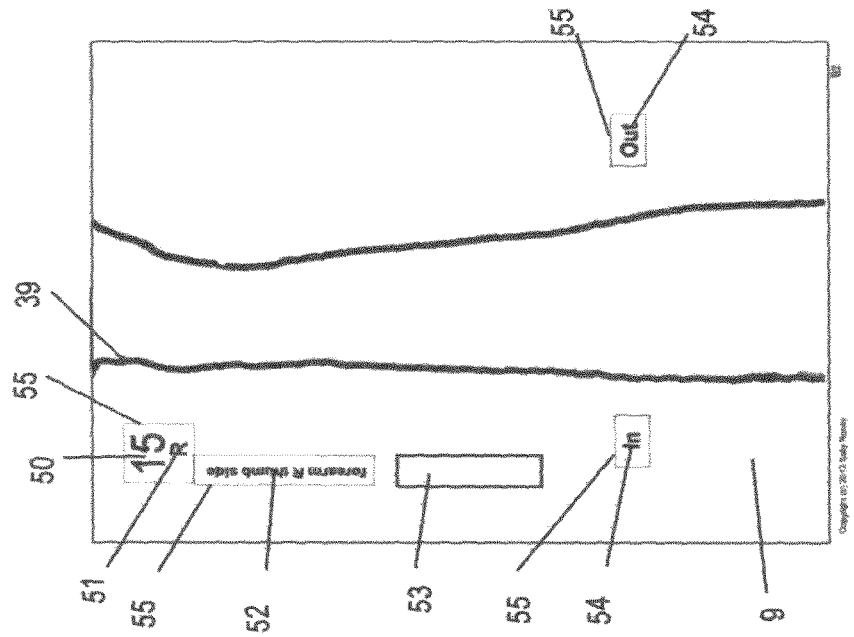
FIG. 18 shows some informational aids on a typical template 9 for labeling and annotations. These appear in digital image 70. These help sorting images 70 and resolve the View Confusion and Mirror Confusion problems.

Using cameras to take close-up photos of body parts to improve resolution loses the context of the body part. However, the camera photos have no option to have automatic labeling. Is this an arm or leg? Is this body part from the right side or left side? Which is the inner surface, which is the outer surface? What is up? What is down? What is view's title what is the view's number? Which ones are easier to sort? FIG. 2, FIG. 18

The large font view numbers help with sorting. In the camera methods too, the home-users sorts many similar digital images of unknown body parts. Most seem to be of the opposite side of the body. This method automatically labels the digital images. Orientation labeling 54 FIG. 18 helps with locating a mole from an image on the body. By automatically labeling the orientation of the body part, moles are easily located. A user can compare each view blissfully unaware of which arm or orientation. However, if something of concern is found they will want to look at it. Then orientation labels 54 will get them to the proper arm and whether near the inner or the outer side of the arm.

Such automatic orienting information is not possible within the image using a camera.

If a camera pulls back to include more contextual information, then the resolution of the digital image drops. Because there are less of the camera's megapixels devoted to that body part or that mole, it produces a ragged zoom and inferior printed images.

Note that the template on the viewfinder of U.S. Pat. No. 7,162,063 is different from template 9 on document scanner 13. U.S. Pat. No. 7,162,063's novel feature, which is the use of the template viewfinder, is not the same as the use of template 9 on scanner 13. Scanner 13 has no display or viewfinder. Glass platen 15 is more like the equivalent of the camera's lens. The template of U.S. Pat. No. 7,162,063 is not intended to be put on the lens of the camera. The semi-transparent image used on the platen would obscure the scanner's image.

The heart of U.S. Pat. No. 7,162,063 method is to create a custom template the user's camera operator fits over his viewfinder so that they can use it to align. Instead, this embodiment provides pre-made pre-labeled outlines 39 for various body types, which in combination with the defined positions; do not need to be customized, as long as they used consistently. Because the images are of smaller portions of body, they have labeling for identification and orientation. U.S. Pat. No. 7,162,063 does not provide for the labeling or orientation. So instead, it is limited to showing sweeping but lower resolution contextual views of the skin. Therefore, scanner 13 is not a simple substitute, since putting labels or invisible instructions on a camera's lens or viewfinder would not achieve the same result. This, and the fact U.S. Pat. No. 7,162,063 is not for solo users, shows it is not being done in the same way. Scanners 13 existed well before the time of U.S. Pat. No. 7,162,063. In addition, U.S. Pat. No. 7,162,063 was not written to include scanners because without the methods described herein, it would not have worked.

Copyright

Templates 9 and transmissible template 9 images that control alignment and image labeling should be patentable in addition to copyrightable because a paper copy of it would not function. Functions include:

Controlling the alignment of the body parts,

Directly producing digital images that are labeled with view numbers and titles and orientation information, Some text is designed to disappear in the digital image, and this is mirrored text for easy cleaning.

This implies templates 9 function in a way different from a paper copy. A paper copy would not be able to control the alignment, label the resulting image, hide some text in the image, nor be a cleanable surface. The alignment required for easy inspection would be inadequate without using outlines 39.

Ways to Hold Scanner 13

How to scan for some body parts, such as the back of hands, is obvious. However, to use scanner 13 to scan the outer portion of the thigh area is not obvious. Trying to lie on top of scanner 13 creates a loud noise and it refuses to scan. Note: most scanners 13 weigh very little.

This embodiment and the following description is for scanners 13 with motor 110 no stronger than needed for level use, and with scanning head 14 with one free end on scanning head 14. Even document scanners 13 which have stronger motors may have greater longevity using these ways to hold. Hold scanner 13 in an orientation such that gravity assists motor 110. If done in the opposite direction, many scanners 13 will stall and click loudly and produce a wavy image. See second embodiment for a vertical scanner. All scanners 13 will stall and click loudly and produce a wavy image with any attempt to lie, or allow excessive weight on scanner 13.

The sound of taps are acceptable during positioning but not while scanning. This is caused by one side of scanning head 14 coming out of its track 20 and hitting glass platen 15. Just tilt scanner 13 to get it back in place. Trying to scan in this position, may cause an unacceptable level of damage to scanner 13.

Figure 7:
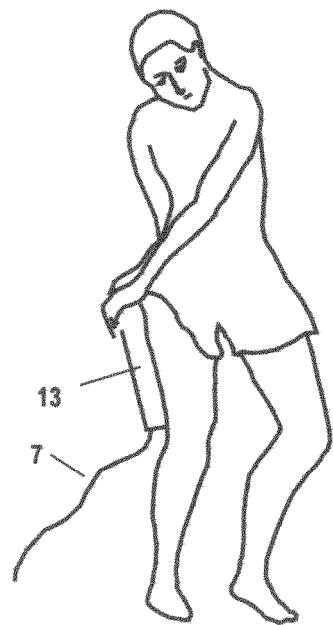
FIG. 7 shows vertical scanning of part of the body that cannot be seen directly.
Figure 9:
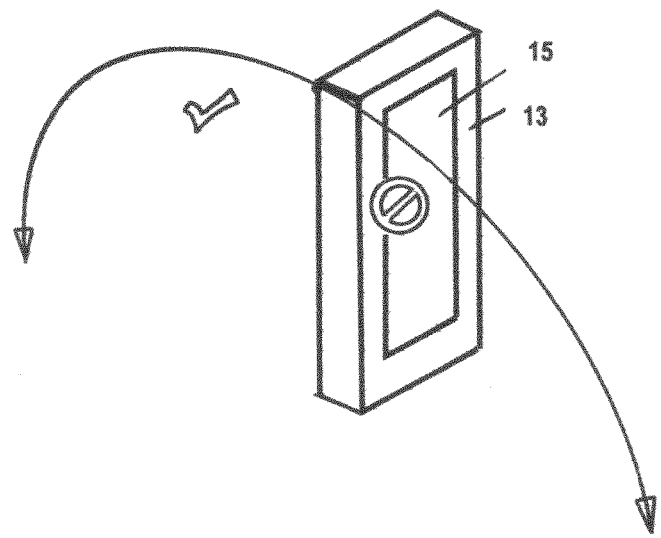
FIG. 9 shows the functional range of orientations of scanner 13 for vertical scanning.

Vertical Orientation FIG. 7 and FIG. 9.

Note: most scanners 13 weigh very little.

The body position varies standing, seated, etc. Scanner 13 is to be held "vertically" pressed against the skin with an almost vertical longitudinal axis. It should be so oriented that scanning head 14 travels downward with gravity. During the scanning head's fast return upwards, do either of the following:

Continue to hold in the vertical position, until scanning head 14 is back safely at the top, or Gently lay scanner 13 flat.

The user knows when scanner 13 is held upside-down because there will be a loud series of destructive noises, and the scan will be distorted by horizontal lines if any scan is possible at all. Additionally for scanners 13 that have a free end of scanning head 14, glass platen 15 should be rotated back slightly to assure that gravity keeps the free end of scanning head 14 in its track 20. User knows when scanner 13 is vertical or tilted downward (incorrect) because there is a loud non-destructive tap during pre-scan positioning.

Body parts that benefit most upper thighs, which otherwise would expose scanner 13 to too much weight.

Parts of the body that cannot be seen with the naked eye can be easily scanned.

The back of the thigh is aligned by viewing from the front.

Optional: use an attached strap if a particular home-user lacks gripping strength to hold scanner 13 in the hands.

Figure 16:
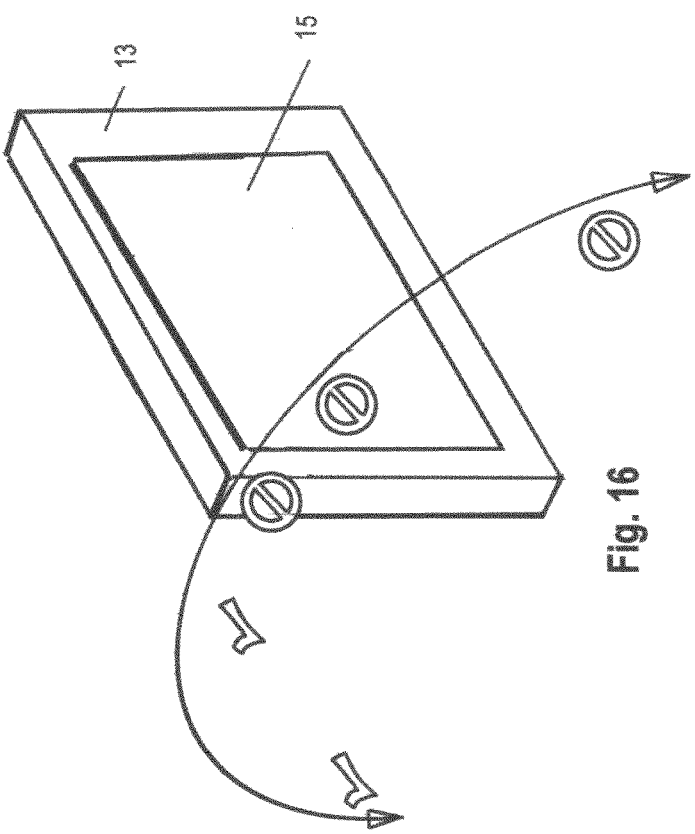
FIG. 16 shows the functional range of orientations of scanner 13 for horizontally upright scanning using scanner 13 with its rail 16 side down.
Figure 14:
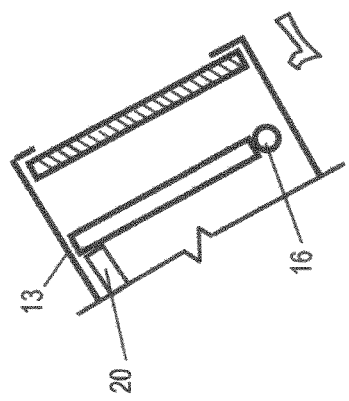
FIG. 14 shows horizontally upright scanning using scanner 13 with its rail 16 side down, scanning head 14 is in a functional orientation with its free end resting in track 20.

Horizontally Upright FIG. 13 or 16

Figure 15:
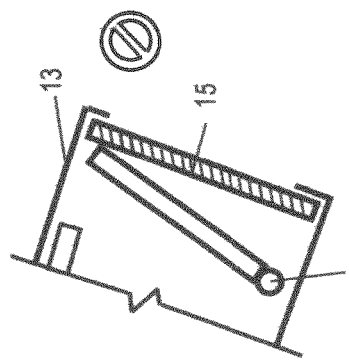
FIG. 15 shows horizontally upright scanning using scanner 13 with its rail 16 side down, it is in a non-functional orientation wherein scanning head 14 hits glass platen 15.

If held "horizontally upright", it may rest on a surface with either of the long sides of scanner 13 down. It can be held upright or at any angle. No need to wait for "scanning head 14" fast return stroke to gently lay scanner 13 flat. However, if a free end of scanning head 14 is at the top, it should be held only at any angle with glass platen 15 tilted upward. This assures that gravity holds the free end of scanning head 14 in its track 20. FIG. 10 or 11. The user knows when scanner 13 is vertical or tilted downward (incorrect) because there is a loud non-destructive tap during pre-scan positioning. FIG. 12 or 15.

A few areas of the middle of the back are aligned by following body Position instructions 40 consistently and using a sensory markers, not shown, on template 9 such as crumpled tape.

Figure 8:
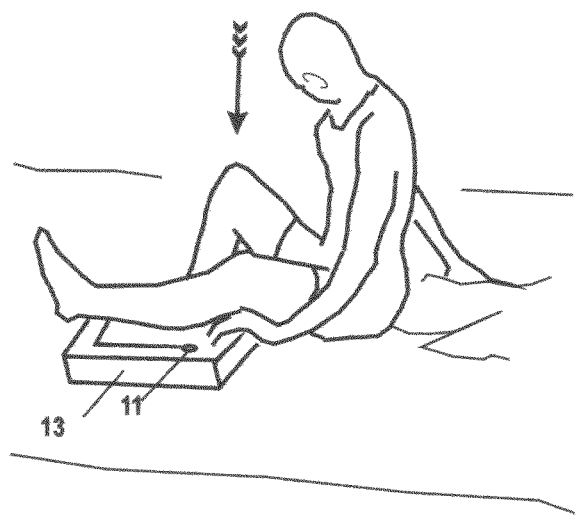
FIG. 8 shows the use of furniture and the case of using scan button 11 on scanner 13.

User Supporting Weight FIG. 8.

Some views of the lower legs and feet can be taken flat on a bed with the user's other leg (see arrow) supporting most of the weight with only light contact on scanner 13. Check for any unusual noises during scanning other than one or two small clicks before lightening the pressure on glass platen 15. Some users would find the outer and front views easier with the vertical method. FIG. 7.

Mounted

Optional Mounting of Scanner 13

Optionally scanner 13 can be mounted or suspended from a holding strap. The sliding mounting bracket provides more options for persons with less mobility or gripping strength. Scanner 13 is hung horizontally upright with scanning head's fixed end upward, if only one end is fixed. FIG. 10. To align their back, user temporarily mounts scanner 13, then uses a mirror to align. Alternatively, a sensory target aligned by feel. The apparatus has a sliding mount whereby scanner 13 can be mounted horizontally on the sliding apparatus, such that it can be adjusted in height for a particular view. In addition, the apparatus can be marked to stop for a particular view. Scanner 13 can be rotated so it is vertically oriented with scanning head 14 scanning downward.

Arbitrary Directions

Many scanners 13 cannot be pointed in arbitrary directions like a camera. Therefore, it is not a simple substitute for a camera because it does not perform the same function in the same way. These scanners 13 must be held in particular ways, whereas a camera has no restriction. Many scanners 13 used as a camera would break, or not function. This shows it is not producing images in the same way.

Scanner 13 is considered a fixed device sitting on a desktop. Many scanners were not engineered to work against gravity. It is not obvious how to scan in unusual orientations. It is only by figuring out how to hold scanner 13, that taking the images of the human body becomes possible. Those ways are not described in U.S. Pat. No. 7,162,063.

Since with scanner 13 the imaging can be done solo, this shows that is not a direct substitution for a camera method that requires a camera operator. Since one method requires two people, and the other requires only one person, it cannot be considered to be done in the same way.

Longevity

Although the first embodiment's method of scanning may invalidate a manufacturer's warranty, many used scanners 13 are available at prices easily affordable for home-users. The first embodiment's method of using scanner 13, while it is probably not good for the scanner's longevity, there are other products that are used in ways not recommended by manufacturers. Many users choose to "over-clock" computer processors even though it invalidates the warranty. Weighing the affordability of scanners 13 and the importance of the intent, while following the restrictions on the method of holding and trying not to drop scanner 13; the home-users should find the risk of a reduced life span of scanner 13 acceptable.

Aids for Operating System Independent Manual Processing of the Images

Aids for manual processing the images are independent of any particular operating system.

Baseline images are intended to be preserved for 20 to 40 years, so they cannot be dependent on any particular computer operating system. The images can be manipulated in a manual mode with basic simple operating system functions, which may change syntax, but will probably always exist. It is assumed that conventional photo editing software is available for the new operating system. The customer independently should be able to create more images for aligned comparison with their old baseline images. At a minimum, they would have access to the images for reference. The software provided for current operating systems mimics these actions.

The baseline and previous digital images are stored in folders on the user's computer 1 named "Viewnumber bodyparttitle". Where Viewnumber is a logical sequence top to bottom and right followed by left. Viewnumber is in large font in each image. A Main folder, named for the user, of folders; where the folders are named "Viewnumber bodyparttitle". The View Number 50 is not the same as the Scan order 30 number. The scans are made in a different order to save time.

Sorting Image Files to Folders

Because of self-labeling, the images are easy to sort into the organized folders. Scan order 30 noted on templates 9 allows scans to be taken in a physically illogical order that saves time during scanning by using the same equipment setup for successive scans. A folder of shortcuts arranged sequentially by Scan order 30 allows the unnamed scans to be easily sorted to the logical view number folders which represent the form of the human body. The shortcuts are named "SO Viewnumber bodyparttitle". Where Viewnumber is View Number 50 and "SO" is an alphabetic code that sorts into the same order as the Scan order 30. Digits are not used so that the only visible number will be the Viewnumber. The folder of sorting shortcuts is sorted by the name of the shortcuts, that is, by Scan order 30. Except for rescans, the images will be scanned in Scan order 30. Rescans can be easily identified since the pattern of opaque reflective shapes 55 in the images is different. Most image thumbnails are dragged consecutively into the shortcuts. Since View Number 50 in the image is of very large font, it may be visible in the thumbnail.

Renaming Files

A text file list of file names is provided. The list's items are in the form "YYMM Viewnumber bodyparttitle.BMP".

Globally replace within the text file the scan's date YYMM in the text file of file names with the current year and date. Cut and paste these names into a search list of recent files BMP, or TIFF, sorted by folder order.

Rotation

Some view images are rotated later so that they can be scanned more easily.

Rotation shortcuts used to identify images that need rotation are in folders named for clockwise, counterclockwise, and 180-degree rotation. These shortcuts take the user directly to the image's folder for systematic rotation with conventional photo editing software (not shown).

Prioritized Comparison

This is a user-customizable folder of shortcuts to the image folders, intended to prioritize comparison of the user's body parts by sun exposure. Where the shortcuts are named "myImportanceRanking Viewnumber bodyparttitle". Where myImportanceRanking is a sortable number. The user can change the sortable name or remove any shortcut to a view that they choose not to make.

Body Map

It is also indexed into diagram of a body that can click through to a folder representing the body part.

To Find a View by Title or View Number

A desktop icon to a folder of shortcuts to the image folders where the shortcuts are named "Viewnumber bodyparttitle"

Shortcuts to the Baseline Images

This folder contains shortcuts to the baseline images. The user's choice of which image should be the baseline for any particular view may change. The shortcuts are named for the image file "YYMM Viewnumber bodyparttitle.BMP".

Software

The software provided for current operating systems mimics the aids for manual processing described above. In addition, there is software for users to make their own customized thumbnail photos 38, and the body map image with hyperlinks mentioned above. There is optional recording of mole dimensions into a database. Conventional consumer photo editing software (not shown) with layers (not shown) is used to display multiple images, and align, if needed. Some conventional consumer photo editing software (not shown) uses different terminology using "object" for what others call "layer". The conventional consumer photo editing software (not shown) can also be used to annotate on transparent overlaying "layers", or by grouping the "objects" representing the annotations.

Realignment

If the user has used outlines 39 according to the directions consistently, the image can be inspected as is. Otherwise, the alignment can be adjusted. Some views are less easy to control. Perhaps outline 39 cannot be seen while the scan is being made. Crumpled tape can allow a sensory clue. However, sometimes the alignment may need realignment with conventional photo editing software (not shown). An easier option is to keep previous images in the layers and compare with one that aligns better.

Enhanced Pale-Blond Chromatic Filter Image 80 (FIG. 22 and FIG. 21)

Optional enhanced pale-blond chromatic filter post processing helps to enhance the contrast between any pale-blond marks and the surrounding flesh colored skin. People in the high-risk age range have many age spots; these should be monitored for growth to differentiate them from pale-blond early melanomas. This is hard to do if the tonal (light-dark) value of the skin is the same as the age spot Optional enhanced pale-blond chromatic filter post processing boosts contrast for moles and helps to differentiate them even in shadow areas. This simplifies the image, not by any diagnostic methods or fractal analysis, but only by chromatically reducing colors other than yellow. A method for post processing a digital image of skin 70 to create an enhanced image 80 comprising filtering said initial digital image 70 by using commercial software to create a yellow separation. Thus, possible moles in shadow are brought into greater contrast and the normal skin pigmentation is reduced. This chromatically modified version of color image as scanned 70 is then made into a grayscale image that aids in the ease of comparison of the images.

This image is perfectly aligned with the color image as scanned 70 from which it is derived. The user has the option to switch between Enhanced image 80 directly overlaying its color image as scanned 70 to assist in preliminary dismissal of obvious non-moles. The user would be warned to look at the color image as scanned to detect blue or red melanomas that would be suppressed in enhanced image 80.

Dimensioning

This is an optional feature. A document scanner's images are innately calibrated, unlike the commonly used visual inspection or photographs. Thus, the images can be used with conventional drawing software (not shown) to dimension the lesions. Such drawing software (not shown) adds text indicating the size to the image.

Diagnostic State Reference

This is an optional feature. The user can ask their dermatologist to mark their moles with removable ink. Then the user scans those locations to make a permanent record of the diagnostics state of their skin. Since these images align with the other images, they can be displayed to reference the diagnostic state of the moles. This is better than a photo of the dermatologist's marks because the diagnosis is displayed in the context of the view. This eliminates the need to look at a photo and interpret where the location would appear in the scanned images.

Optionally this diagnostic state can be aligned exactly with the baseline image, and the diagnostic marks transferred by manually annotating to a new transparent layer of the conventional photo editing software (not shown). These marks would be the choice of the user. For example: a red circle with a 4-digit number might indicate View Number 50 and a 2-digit ID code. The red could indicate that the dermatologist diagnosed the mole. A yellow circle might indicate a slightly suspicious spot found by the user that should be shown to the dermatologist at the next visit.

Body Map

The body map gives easy reference to the baseline images. A diagram of a body is divided into views with hyperlinks that display the baseline images. The body map provides a permanent graphic reference for whether a mole is new or pre-existing.

Operation-First Embodiment

Introduction

This is a practical method, even for solo home-users without a partner, to image even areas that cannot be seen directly. These areas include the back, back of upper arms, back of thighs, and other areas frequently exposed to the sun. The user creates a baseline set of images. Later compares them to current images to check for growth or changes. Alternatively, the user takes only the baseline images and may use them with a body map to quickly check if a casually noticed lesion is new or pre-existing. The home-user also has the option to decide how much of the body to image, whether just the swimsuit exposed areas or less. Also has the option to do some views more frequently than other views. The method is very flexible for home-users.

I presently contemplate for this embodiment, using computer screen 3 to compare the images. Many different screen 3 units are possible, such as television, tablet 102, or phone. These are covered as alternate embodiments.

Setup

Scanner lid 4*a* or 4*b* is removed. FIG. 6. Most scanner lids 4*a* or 4*b* are removable; the others are easily cut at hinges 5*a* or 5*b*.

Position instructions 40 FIG. 17 on template 9 are readable because they are backlit while on scanner 13 FIG. 4. Instruction text disappears because lid 4*a* or 4*b* of scanner 13 has been removed and the instruction text will disappear into the blackness surrounding the body part in the image. If possible, avoid pointing scanner 13 at a bright overhead light or window. This makes a bright area around the body part and the instructions do not completely disappear.

Scanners 13 of this embodiment that have motor 110 unable to scan against gravity: The first time using that scanner 13 determine the direction the movable scanning head 14 FIG. 5 scans downward with gravity. If the user tries it in the opposite direction, it will stall, click loudly, and produce a wavy image. Label correct direction on the scanner's case. If scanner 13 has a built-in carrying handle 12 FIG. 4, it will likely be on the wrong end such that scanning head 14 FIG. 5 travels upward against gravity.

Ignore this step for scanners with two rails 17 FIG. 5: Determine the side where movable scanner head 14 FIG. 5 is attached. This is usually a metal rod or other longitudinal continuous part running on one side of scanner 13 and visible through glass platen 15. Label that on the scanner's case.

The desired resolution is set, 300 spi is a good minimum. If necessary, the scanner's software driver is set to use scanner's button 11 FIG. 4. Optionally computer screen 3 can display small pictures of the images as they are saved.

Scanning

Template 9 FIG. 4 is taped with removable tape 10 FIG. 4 to glass platen 15 FIG. 6 of scanner 13 FIG. 4. Apply a sensory target to template 9 if so instructed. The user positions their body following printed position instructions 40 on template 9. Scanner 13 is put in the described position and the body part is aligned in outline 39. The muscles are relaxed as much possible for better contact with glass platen 15.

How to Use and Hold Scanner 13

All scanners 13 will stall and click loudly and produce a wavy image with any attempt to lie, or allow excessive weight on scanner 13. The sound of taps are acceptable during positioning but not while scanning. This is caused by one side of scanning head 14 coming out of its track 20 and hitting glass platen 15. Just tilt scanner 13 to get it back in place. Trying to scan in this position, may cause an unacceptable level of damage to scanner 13.

Vertical Orientation FIG. 7.

Note: most scanners 13 weigh very little.

The body position varies standing, seated, etc. Scanner 13 is to be held "vertically", pressed against the skin with an almost vertical longitudinal axis. FIG. 9. It should be so oriented that scanning head 14 travels downward with gravity. During the scanning head's fast return upwards, do either of the following:

Continue to hold in the vertical position, until scanning head 14 is back safely at the top, or Gently lay scanner 13 flat.

The user knows when scanner 13 is held upside-down because there will be a loud series of destructive noises, and the scan will be distorted by horizontal lines if any scan is possible at all. Additionally for scanners 13 that have a free end of scanning head 14, glass platen 15 should be rotated back slightly to assure that gravity keeps the free end of scanning head 14 in its track 20. FIG. 12. The body can be swayed to accomplish this. User knows when scanner 13 is vertical or tilted downward (incorrect) because there is a loud non-destructive tap during pre-scan positioning. FIG. 12.

Body parts that benefit most: upper thighs, which otherwise would expose scanner 13 to too much weight.

Parts of the body that cannot be seen with the naked eye can be easily scanned. The back of the thigh is aligned by viewing from the front.

Optional: use an attached strap if a particular home-user lacks gripping strength to hold scanner 13 in the hands.

Horizontally Upright FIG. 13 and FIG. 16

If held "horizontally upright", scanner 13 may rest on a surface with either of the long sides of scanner 13 down. It can be held upright or at any angle with glass platen 15 tilted upward. There is no need to wait for scanning head's fast return stroke to gently lay scanner 13 flat. However, if a free end of scanning head 14 is at the top, it should be held only at any angle with glass platen 15 tilted upward, not vertically. This assures that gravity holds the free end of scanning head 14 in its track 20. User knows when scanner 13 is vertical or tilted downward (incorrect) because there is a loud non-destructive tap during pre-scan positioning. FIG. 12 or 15.

A few areas of the middle of the back are aligned by following body Position instructions 40 consistently and using a sensory markers on template 9 such as crumpled tape.

User Supporting Weight FIG. 8.

Some views of the lower legs and feet can be taken flat on a bed with the user supporting most of the weight of the leg with only light contact on scanner 13. Check for any unusual noises during scanning other than one or two small clicks before the user can lighten the pressure on glass platen 15. Some users would find the outer and front views easier with the vertical method.

There are two areas of high concave or convex curvature that do not make good contact with flatbed scanner 13. These areas are the front view of the neck, and the top view of the shoulders. The areas can be scanned, but the quality is not good with the full-size flatbed scanner 13. Fortunately, these areas are easily visible to the user in a mirror. Alternately, a hand-held document scanner could be used.

Comparison

Although the difference between age spots and pale-blond moles are not visible to an untrained home-user, moles can grow and the age spot cannot grow. Therefore, the layperson does not need to be able to diagnose the difference. All they have to detect is a lesion getting larger. If in doubt, the user can zoom in for details. If they find a suspicious growing lesion, they can rescan just the immediate area of the lesion at even higher resolution and monitor it more often. They can print out the current and the baseline images for their dermatologist.

"Spot" refers to a mark in an image that is not yet diagnosed. If it never grows or changes, there is no need to diagnose it. It may be a mole or lesion or a scar.

Layered enhanced pale-blond chromatic filter versions of the aligned baseline and current images are displayed on screen 3 such that a mouse 8 click displays the other image. Layered conventional photo editing software (not shown) is like a child's flipbook. The natural ability of the human mind to detected motion sees this as frames of a movie with an object in motion. The user observes the spots without concern for whether they are of the baseline or the current image.

Since all images are at the same scale, groups of spots form identifiable constellations in motion. A "constellation" is a localized group of spots that are not so numerous that they are confusing. The mind can perceive a single, a pair, a triangle, a constellation of three, or a quadrilateral constellation of four, or a lack of any. If there are too many spots, the user can increase the zoom to simplify the image.

The constellations of spots are seen to move. The user checks if any spots in the constellations appear or grow. Since the rest of the constellation identifies each mole within the constellation, there is no need to individually identify or locate on the body any particular lesion within the constellation. That makes it practical to examine the many views of the body at such high magnification over most exposed surface of the body.

"Close enough" alignment is needed because just as in a movie that has a damaged section cut out, one sees an actor on one side of screen that is suddenly on the other side of the screen and then one thinks it is a different person. The same thing happens with bad alignment. If they are close enough, it is perceived as motion of an identical object. If it is too far out of alignment, it is perceived as a separate object and slows the process. Without the template's outline 39s and instructions, rotation and twisting of various body parts would produce different views that could not be aligned. Generally, current and baseline spots do not all line up one over the other. This is not a problem since our minds naturally see patterns moving. Generally, the alignment of a quickly taken scan is "good enough". Because of "close enough" alignment, constant realignment is not needed because the lesions do not have to overlay each other.

Alternately, any method of comparison could be used.

Since the views are of smaller areas, unlike distant camera views, if needed, one alignment is "close enough". Not only are there less spots to align, but there are less joints, hence less degrees of freedom. This "close enough" alignment is good enough for the whole view, unlike the blinking method of U.S. Pat. No. 7,162,063 that requires frequent realignment so that the spots overlay each other.

Game

Two optional computer games are possible. Firstly, there could be a simple game to make comparison more fun. This game could be "outsourced" to children. Another possibility would be a professionally designed Internet game where altruistic gamers may want to play. Inverted and filtered enhanced pale-blond chromatic filter images 80 look like planets in space.

Magnification FIG. 1

If scanner 13 were set to only 300 spi (samples per inch), it would print a full size photo at 100% magnification. A 3.2 mm or ⅛-inch mole would be shown as A 3.2 mm or ⅛ inch in the printed photo. That 2.54 cm or one inch of skin would appear on that screen 3 as 3 cm or 3.1 inches. FIG. 1.

If scanner 13 were set to 1200 spi, it would print a full size photo at 400% magnification. A 3.2 mm or ⅛-inch mole would be shown as 12.8 mm or a half-inch in the printed photo. There are intermediate settings that a visually compromised user could choose. The high-risk age group middle aged to elderly; typically includes those with bad close vision. Many scanners 13 can be set to scan at higher samples per inch (i.e. more magnification) than even people with visual acuity problems would need. Although a user would not choose to use such very high resolution for all scans, it is helpful to have that option for suspected lesions.

Dermatologist

If there is a new or larger spot that the user wants to show their dermatologist, they can print the baseline image and the current image as photos. They will automatically be at the same scale. If a greatly magnified photo is desired, scanner 13 can be set to its maximum optical resolution. Even an old scanner 13 can have an optical resolution of 1200 dpi. Which can produce a true 400% magnified printed image. If a home-user is unsure of a "spot", they can rescan to monitor that view or detail at a high magnification FIG. 1 at more frequent intervals until they decide whether to show the dermatologist. They may choose to use the dimensioning feature with these images.

Optionally the user can ask their dermatologist to mark their moles with removable ink. This is described as Diagnostic State Reference above.

DETAILED DESCRIPTION

Second Embodiment

This embodiment is for any device that can image a surface while in contact, in arbitrary orientations, and has an imaging surface for a useful-sized template. An example is: U.S. Pat. No. 7,104,450. Vertical flatbed document scanners like this may be made with stronger motors to aid in the use in different orientations; and with track 20 modifications that would aid in different orientations. However, this embodiment also includes any device that can image a surface while in contact, whether or not it is called a "scanner", or uses an imaging acquisition method other than scanning head 14 FIG. 5. It is not a handheld dermatology scanner with the usual lemon-sized imaging surface.

Devices of this embodiment would not require all the special way to hold a scanner as described for the first embodiment. However, excessive weight on any device would always be a concern. Devices using scanning heads 14 object to excessive weight on the device and will stall and click loudly and produce a wavy image. FIG. 7 and FIG. 8.

This is how the user would know if a device can acquire images in arbitrary orientations.

While not scanning, tilt the imaging surface downward; if there is no tap sound, continue. Hold scanner 13 in various directions and try to image, if it does not stall, click loudly, and produce a wavy image it can acquire images in arbitrary orientations.

DETAILED DESCRIPTION

Fourth Embodiment

This embodiment is for any device that can display images 70 80 created by the other embodiments. Users can compare these images on their choice of display devices including but not limited to: other desktop computer screen 3, laptop computers 3b, tablet computers 102, television, phones, PDA, and any other display devices. Software would take full-sized images and display them on a Smartphone, tablet computer 102 or other smaller display device in smaller pieces. Software would allow zooming, and the switching between baseline and current images. Software would also keep track of which views have been compared.

DETAILED DESCRIPTION

Fifth Embodiment

This embodiment covers templates 9's two-sided use, mirrored text FIG. 19 for cleanability, disappearing instructions 112, the specific types of aids, including media, labeling and annotations on the images as well as their electronic transmission so templates 9 can be printed. The templates of this embodiment are not limited to the use of skin imaging. For example, they could be used to align objects.

DETAILED DESCRIPTION

Sixth Embodiment

Services

This embodiment adds some or all of these features more appropriate for free or fee-for-services:

Human-sized clear surface with an assistant and a plurality of scanners 13 below.

Mounted devices as covered in the Optional Mounting of the Scanner section of the first embodiment.

Services for the alignment of images.

Services for the enhanced pale-blond chromatic filter of images.

Services for the dimensioning of moles in images.

DETAILED DESCRIPTION

Seventh Embodiment

This embodiment covers providing described enhanced pale-blond chromatic filter post processing for submitted images, made by any process including cameras.

Optional enhanced pale-blond chromatic filter post processing helps to enhance the contrast between any pale-blond marks and the surrounding flesh colored skin. This simplifies the image by chromatically reducing colors other than yellow. Thus, possible moles in shadow are brought into greater contrast and the normal skin pigmentation is reduced. This chromatically modified version of color image as scanned 70 is then made into a grayscale image that aids in the ease of comparison of the images. A method for post processing a digital image of skin 70 to create an enhanced image 80 comprising filtering said initial digital image 70 by using commercial software to create a yellow separation. This image is perfectly aligned with color image as scanned 70 from which it is derived. The user has the option to switch between Enhanced image 80 directly overlaying its color image as scanned 70 to assist in preliminary dismissal of obvious non-moles. The user would be warned to look at color image as scanned 70 to detect blue or red melanomas that would be suppressed in enhanced pale-blond chromatic filter images 80.

DETAILED DESCRIPTION

Eighth Embodiment

This embodiment is for any device that can image a surface while in contact, and has an imaging surface where a useful-sized template could be mounted. Method of orienting scanner 13 is used. Images are taken without any template 9, FIG. 16. Images have no instructions or labeling.

While the above description contains many specificities, these should not be construed as limitations on the scope of any embodiment, but as exemplifications of various embodiments thereof. Many other ramifications and variations are possible within the teachings of the various embodiments. For example, the templates could vary the aids and labels and annotations, or locate them differently. Not all views require the same labels. It would be easy to add a useful aid, or eliminate a nonessential one. Some views can be made in different positions. The enhanced pale-blond chromatic filter could be tweaked, but it still would rely on the idea that blond and brown are yellow and blood is not. Thus, the scope should be determined by the subsequent claims and their legal equivalents, and not by the examples given.

I claim:

1. A method of enabling a solo home user to identify new or significantly changed skin lesions for the purpose of detecting possible melanomas, comprising:
  (a)
  i) holding a maneuverable device selected from the group consisting of:
    1) a flatbed document scanner wherein a lid of said flatbed document scanner has been removed, and said flatbed document scanner is oriented so that a motor thereof is not pulling against gravity and a scanning head thereof is not dropping out of a track thereof and a glass platen thereof is not exposed to pressure which would cause it's motor to stall, or
    2) a vertical flatbed document scanner wherein a lid of said vertical flatbed document scanner has been removed and said vertical flatbed document scanner is oriented so that a glass platen thereof is not exposed to pressure which would cause it's motor to stall,
  ii) attaching one of a plurality of view-specific templates to said glass platen of said maneuverable device and said template containing text and graphics to be viewed while scanning and wherein automatic labeling to be included in said digital images are printed and said template has backings of opaque reflective shapes on the upper surface and where said automatic labeling to be included in said digital images are printed on the undersurface, and
  iii) aligning the user's body by referring to scanning and alignment aids of said text and graphics of said template including view-specific orientations and directions for control of workflow, and
  iv) providing said plurality of view-specific templates to make a plurality of digital images representing a plurality of views of portions of the body, whereby said solo home user can create aligned high resolution images of their own body in privacy without a photographer and further can zoom in to find, magnify, measure and document skin lesions even on parts of their bodies they cannot see directly and further forming a record of said skin lesions and locations currently without said skin lesions and further said view-specific scanning and alignment aids are automatically obscured in said digital images and further said digital images are automatically calibrated, and automatically labeled with view-specific information from said template which solves view confusion and mirror confusion.

2. The method of claim 1 further comprising transmitting over the Internet said view-specific scanning and alignment aids and said automatic labeling including video and audio as well as said text and graphics and further wherein said maneuverable device is said flatbed document scanner, said text, graphics, and said automatic labeling are printed on transparent film for use as said templates and further wherein said video and audio are installed on a computer connected to said flatbed document scanner.

3. The method of claim 1 further comprising providing said view-specific templates for various body types.

4. The method of claim 1 further comprising providing software for comparing said digital images with an earlier baseline image on a tablet computer or a personal computer or a smaller mobile display-only device.

5. The method of claim 1 further comprising
(a) providing
(i) at least one initial digital image
(ii) running software to create a yellow separation of the initial digital image
whereby pale-blond pre-melanomas and presumed age spots of the same light-dark value as the surrounding flesh color or hidden in shadows can be easily discerned however red or blue pre-melanomas would not be visible.

6. The method of claim 5 wherein if the software creating said yellow separation does not automatically create a grayscale image then running said software to convert said yellow separation to grayscale.

7. The method of claim 1 further comprising
(a) providing
(i) at least one view's digital initial image and
(ii) at least one follow up digital image of the same view of said solo home user's skin, wherein said follow up digital image is taken at a later time than said initial digital image; and
(iii) comparing said initial digital image and said follow up digital image to identify any new or changed moles or lesions.

8. The method of claim 1 further comprising providing said template that has an underside containing said text and graphics wherein said scanning and alignment aids to be viewed while scanning is printed in mirrored text and mirrored graphics and wherein said automatic labeling to be included in said digital images are printed without mirroring.

9. A method for post processing a digital image of skin with a chromatic filter to create an enhanced image that increases the contrast of pale-blond pre-melanomas and presumed age spots relative to flesh color, comprising:
(a) providing at least one digital image of skin from a source, and
(b) filtering said digital image by:
(i) running software to create a yellow separation
whereby the pale-blond pre-melanomas and the presumed age spots of the same light-dark value as the surrounding flesh color or hidden in shadows can be easily discerned however red or blue pre-melanomas would not be visible.

10. The method of claim 9 wherein if the software creating said yellow separation does not automatically create a grayscale image then running said software to convert said yellow separation to grayscale.

11. A method of enabling a solo home user to image and measure spots on their body they cannot see directly for the purpose of detecting possible melanomas, comprising:
i) holding a maneuverable device selected from the group consisting of:
1) a flatbed document scanner wherein a lid of said flatbed document scanner has been removed, and said flatbed document scanner is oriented so that a motor thereof is not pulling against gravity and a scanning head thereof is not dropping out of a track thereof and a glass platen thereof is not exposed to pressure which would cause it's motor to stall, or
2) a vertical flatbed document scanner wherein a lid of said vertical flatbed document scanner has been removed and said vertical flatbed document scanner is oriented so that a glass platen thereof is not exposed to pressure which would cause it's motor to stall,
ii) attaching a template to the glass platen which includes a view number thereon,
iii) orienting said maneuverable device on the solo home user's body, and
iv) making a plurality of digital images representing a plurality of views of portions of the body whereby said solo home user can create unaligned high resolution images of their own body in privacy without a photographer and further can zoom in to find, magnify, measure and document skin lesions on parts of their bodies they cannot see directly and further forming a non-aligned baseline record of said skin lesions and locations currently without said skin lesions and; further said digital images are automatically calibrated; although they are unaligned images.

12. The method of claim 11 further comprising providing a computer program to superimpose view-specific template labeling onto said digital images.

13. The method of claim 11 further comprising
(a) providing at least one initial digital image, and
(b) running software to create a yellow separation on the at least one initial digital image,
whereby pale-blond pre-melanomas and presumed age spots of the same light-dark value as the surrounding flesh color or hidden in shadows can be easily discerned however red or blue pre-melanomas would not be visible.

14. A The method of claim 13, wherein if the software creating said yellow separation does not automatically create a grayscale image then running said software to convert said yellow separation to grayscale.

15. A method for using templates for embedding automatic labeling appearing in captured digital images while scanning malleable or flat-sided objects, comprising:
i) providing a document scanner, removing a lid of the scanner, and providing one of a plurality of said templates, said template containing text and graphics to be viewed while scanning and wherein said automatic labeling to be included in said digital images are printed on the templates, and said template has backings of opaque reflective shapes on the upper surface, where said automatic labeling to be included in said digital image are printed on the undersurface, and aligning said objects by referring to scanning and alignment aids, including directions for control of workflow, included in said text and graphics of said template, further providing said plurality of said templates to make a plurality of said digital images representing a plurality of views of inventories or collections of said malleable or said flat-sided objects, whereby said scanning and alignment aids are automatically obscured in said digital images and further said digital images are automatically labeled with said automatic labeling from said template.

16. The method of claim 15 further comprising providing said templates with said undersurface containing said text and graphics wherein said scanning and alignment aids to be viewed while scanning are printed in mirrored text and mirrored graphics and wherein said automatic labeling to be included in said digital images are printed without mirroring, whereby only unregistered one-sided printing is necessary and said template's upper surface can be cleaned without removing the printing.

* * * * *